(12) United States Patent
Chin et al.

(10) Patent No.: US 11,564,797 B2
(45) Date of Patent: Jan. 31, 2023

(54) VENOUS VALVE PROSTHESIS

(71) Applicant: Innovein, Inc., Santa Rosa, CA (US)

(72) Inventors: Albert K. Chin, Palo Alto, CA (US); Austin Walker, Hillsborough, CA (US); Thomas A. Kramer, San Carlos, CA (US)

(73) Assignee: Innovein, Inc., Santa Rosa, CA (US)

( * ) Notice: Subject to any disclaimer, the term of this patent is extended or adjusted under 35 U.S.C. 154(b) by 129 days.

(21) Appl. No.: 16/276,158

(22) Filed: Feb. 14, 2019

(65) Prior Publication Data
US 2019/0175347 A1 Jun. 13, 2019

Related U.S. Application Data

(63) Continuation of application No. 15/247,523, filed on Aug. 25, 2016, now Pat. No. 10,231,838.
(Continued)

(51) Int. Cl.
*A61F 2/24* (2006.01)
*A61F 2/91* (2013.01)

(52) U.S. Cl.
CPC .......... *A61F 2/2475* (2013.01); *A61F 2/2424* (2013.01); *A61F 2/2427* (2013.01);
(Continued)

(58) Field of Classification Search
CPC .... A61F 2/2475; A61F 2/2424; A61F 2/2427; A61F 2250/0092; A61F 2/24; A61F 2250/006; A61F 2250/0059; A61F 2250/0062; A61F 2250/0003; A61B 1/3137
See application file for complete search history.

(56) References Cited

U.S. PATENT DOCUMENTS

| 3,466,671 A | 9/1969 | Siposs |
| 3,593,343 A | 7/1971 | Viggers |

(Continued)

FOREIGN PATENT DOCUMENTS

| CN | 103313681 A | 9/2013 |
| CN | 104427956 A | 8/2015 |

(Continued)

OTHER PUBLICATIONS

European Search Report for Application No. 16840136.2 dated Mar. 19, 2019, 9 pages.
(Continued)

*Primary Examiner* — Brian E Pellegrino
(74) *Attorney, Agent, or Firm* — Knobbe, Martens, Olson & Bear LLP

(57) ABSTRACT

A venous valve prosthetic implant for treatment of venous disease may include an expandable anchoring frame, a valve seat attached to the anchoring frame, a ball retention member attached to the anchoring frame, and a ball disposed within the lumen of the anchoring frame, between the valve seat and the ball retention member. The anchoring frame may include a first end, a second end, and a middle valve portion, where the middle valve portion expands to a smaller diameter than a diameter of either the first end or the second end. The ball may move back and forth within the middle valve portion, between a fully open position and a fully closed position.

22 Claims, 24 Drawing Sheets

Related U.S. Application Data

(60) Provisional application No. 62/356,337, filed on Jun. 29, 2016, provisional application No. 62/209,351, filed on Aug. 25, 2015.

(52) U.S. Cl.
CPC .......... *A61F 2/91* (2013.01); *A61F 2210/009* (2013.01); *A61F 2230/001* (2013.01); *A61F 2250/0039* (2013.01); *A61F 2250/0067* (2013.01)

(56) References Cited

U.S. PATENT DOCUMENTS

| | | | |
|---|---|---|---|
| 3,626,518 A * | 12/1971 | Leibinsohn | A61F 2/2424 623/2.35 |
| 3,890,968 A | 6/1975 | Pierce | |
| 3,911,502 A | 10/1975 | Boretos | |
| 4,030,520 A | 6/1977 | Sands | |
| 4,922,905 A | 5/1990 | Strecker | |
| 5,146,933 A | 9/1992 | Boyd | |
| 5,332,402 A | 7/1994 | Teitelbaum | |
| 5,397,351 A | 3/1995 | Pavcnik | |
| 5,697,968 A | 12/1997 | Rogers et al. | |
| 5,810,847 A | 9/1998 | Laufer | |
| 5,989,276 A | 11/1999 | Houser et al. | |
| 6,066,088 A | 5/2000 | Phillip | |
| 6,293,955 B1 | 9/2001 | Houser | |
| 6,299,637 B1 | 10/2001 | Shaolian | |
| 6,315,793 B1 | 11/2001 | Bokros | |
| 6,440,164 B1 | 8/2002 | DiMatteo | |
| 7,112,220 B2 | 9/2006 | Houston | |
| 7,435,257 B2 | 10/2008 | Lashinski et al. | |
| 7,449,027 B2 | 11/2008 | Hunt | |
| 7,955,346 B2 | 6/2011 | Mauch | |
| 8,167,928 B2 | 5/2012 | Melzer | |
| 8,246,676 B2 | 8/2012 | Acosta | |
| 8,377,115 B2 | 2/2013 | Thompson | |
| 8,425,550 B2 | 4/2013 | Elliott et al. | |
| 8,617,238 B2 | 12/2013 | Palmaz | |
| 8,956,405 B2 | 2/2015 | Wang | |
| 9,622,862 B2 | 4/2017 | Lashinski et al. | |
| 9,737,422 B2 | 8/2017 | Armstrong | |
| 10,231,838 B2 | 3/2019 | Chin | |
| 10,492,910 B2 | 12/2019 | Kirk et al. | |
| 10,912,647 B2 | 2/2021 | Chin et al. | |
| 10,973,640 B2 | 4/2021 | Argentine et al. | |
| 11,000,376 B2 | 5/2021 | Chanduszko | |
| 11,083,583 B2 | 8/2021 | Kirk et al. | |
| 11,285,243 B2 | 3/2022 | Jaffe | |
| 2004/0210304 A1 | 10/2004 | Seguin | |
| 2004/0210307 A1 | 10/2004 | Khairkhahan | |
| 2005/0182483 A1 | 8/2005 | Osborne et al. | |
| 2005/0278023 A1 | 12/2005 | Zwirkoski | |
| 2006/0074483 A1 * | 4/2006 | Schrayer | A61F 2/2412 623/2.1 |
| 2007/0100435 A1 | 5/2007 | Case et al. | |
| 2007/0293808 A1 | 12/2007 | Williams | |
| 2008/0249611 A1 | 10/2008 | Melzer | |
| 2009/0105823 A1 | 4/2009 | Williams et al. | |
| 2010/0057192 A1 | 3/2010 | Celermajer | |
| 2012/0265186 A1 | 10/2012 | Burger et al. | |
| 2013/0131780 A1 | 5/2013 | Armstrong | |
| 2013/0231736 A1 | 9/2013 | Essinger et al. | |
| 2014/0018935 A1 | 1/2014 | Wang | |
| 2014/0379074 A1 | 12/2014 | Spence et al. | |
| 2015/0142103 A1 * | 5/2015 | Vidlund | A61F 2/2418 623/2.17 |
| 2016/0338834 A1 | 11/2016 | Eckberg | |
| 2017/0056175 A1 | 3/2017 | Chin | |
| 2019/0343623 A1 | 11/2019 | Chau et al. | |
| 2021/0186700 A1 | 6/2021 | Chin et al. | |
| 2021/0369459 A1 | 12/2021 | Ehnes et al. | |

FOREIGN PATENT DOCUMENTS

| | | |
|---|---|---|
| DE | 19509464 | 6/1996 |
| DE | 19619089 | 11/1997 |
| JP | H05-269192 A | 10/1993 |
| JP | 2001-503657 A | 3/2001 |
| JP | 2002-520087 A | 7/2002 |
| JP | 2013-208458 A | 10/2013 |
| RU | 2332960 C1 | 9/2008 |
| SU | 1507369 | 9/1989 |
| WO | 2007127477 | 11/2007 |
| WO | WO2017035372 A1 | 3/2017 |

OTHER PUBLICATIONS

International Search Report and Written Opinion for PCT/US2016/048729, dated Nov. 18, 2016, 14 pages.
International Preliminary Report on Patentability for PCT/US2016/048729, dated Feb. 27, 2018, 8 pages.
Casa et al., Role of high shear rate in thrombosis. J Vasc Surgery (2015) 61(4): 1068-1080.
Mehrabadi, et.al, A Predictive Model of High Shear Thrombus Growth, Annals of Biomedical Engineering (2016) 44: 2339-2350.
Amrane et al., Starr-Edwards aortic valve: 50+ years and still going strong: A case report. Eu Heart J.—Case Reports (2017) 1: 1-3.
Gott et al., Mechanical heart valves: 50 years of evolution. Ann Thorac Surg. (2003) 76: 2230-2239.
Saxena et al., Starr-Edwards aortic valve: Forty-four years old and still working! J Thora Cardiovas Surg. Oct. 1, 2013;146(4): e21-22.

* cited by examiner

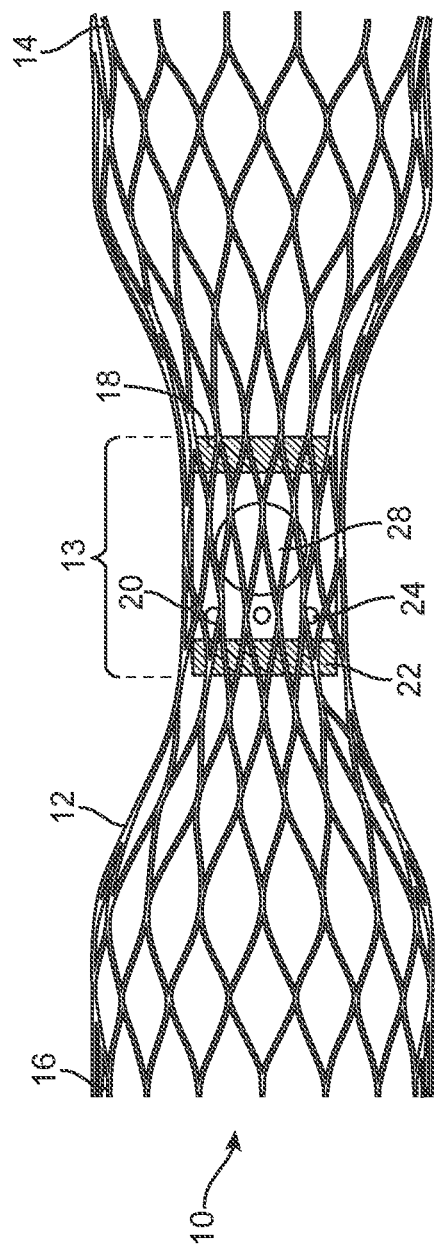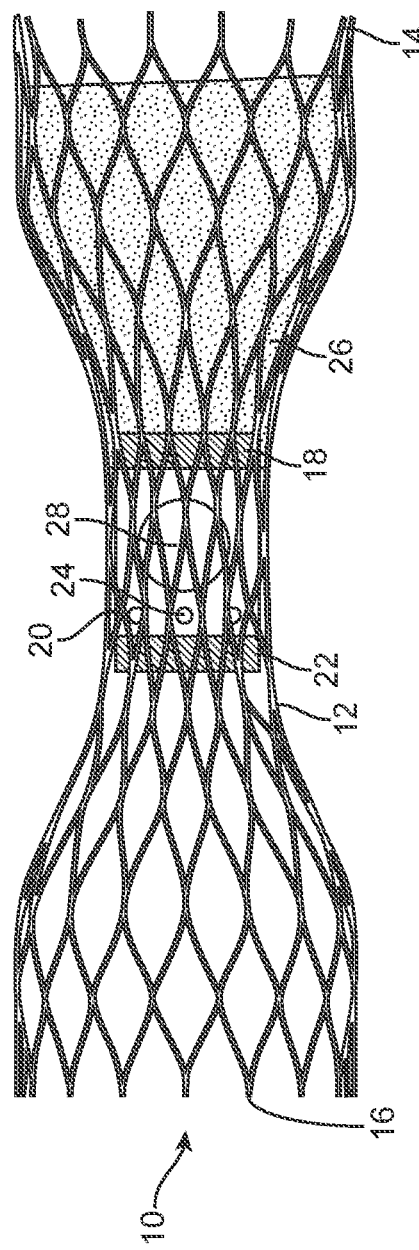
FIG. 1A
FIG. 1B

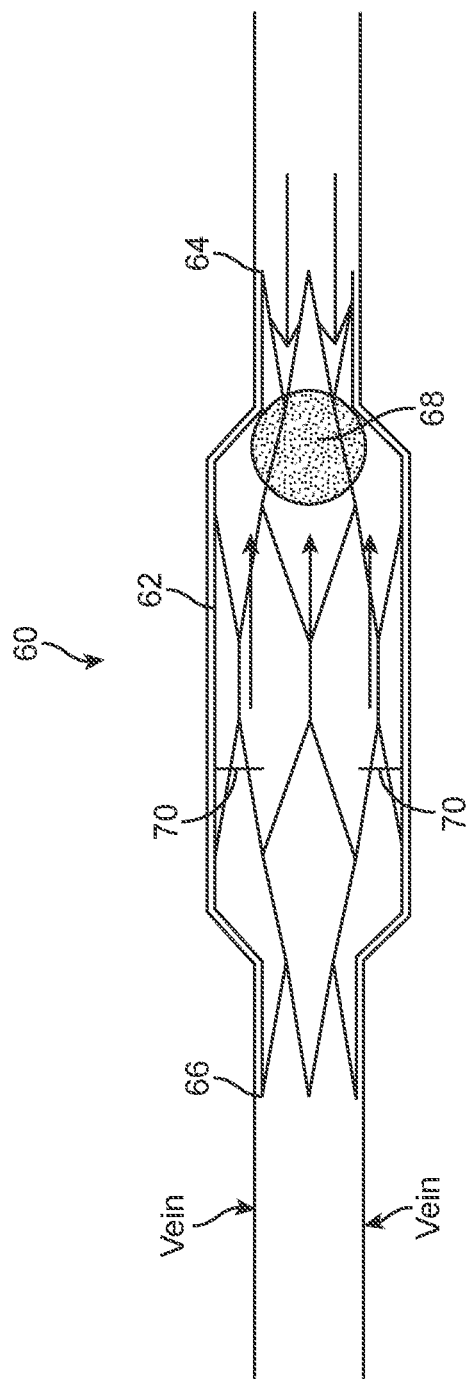
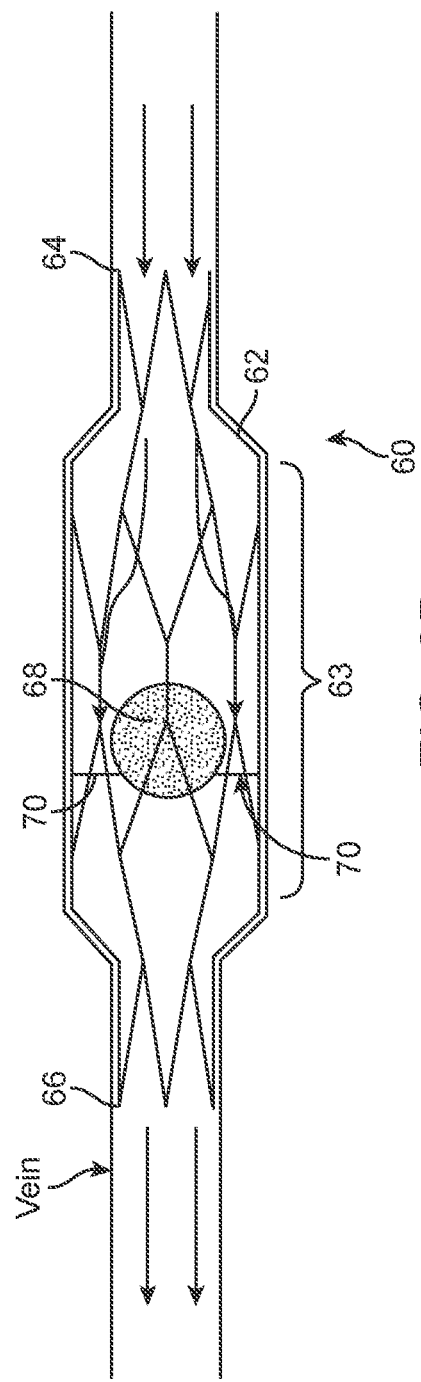
FIG. 8A
FIG. 8B

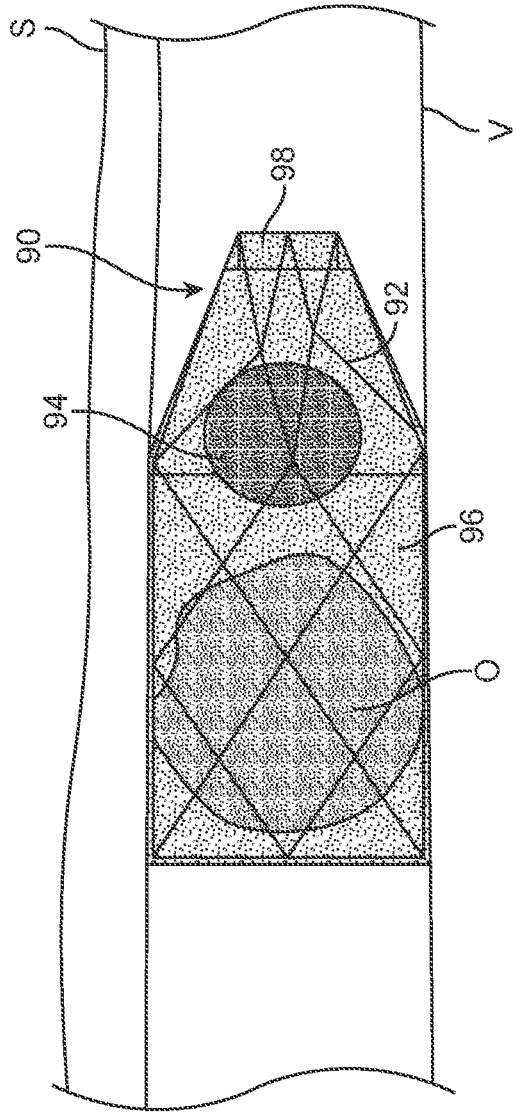
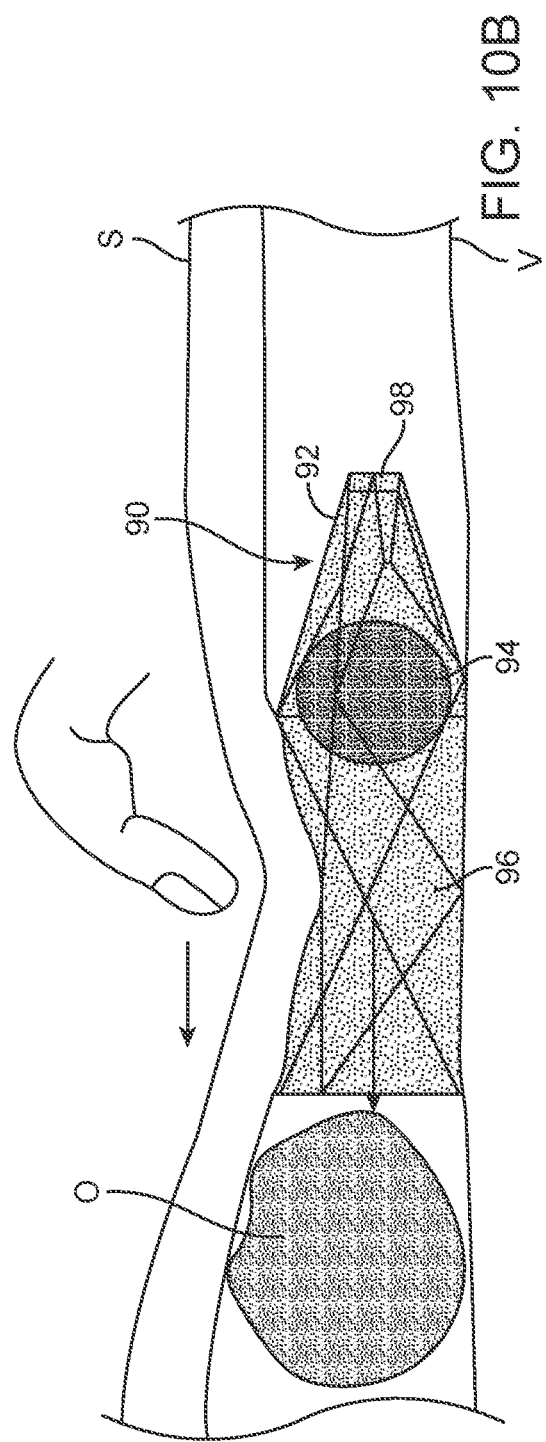
FIG. 10A
FIG. 10B

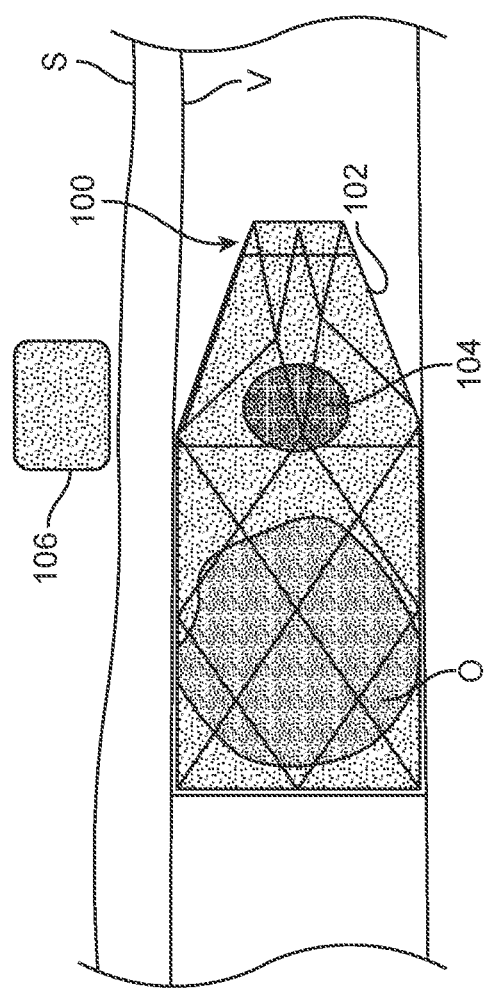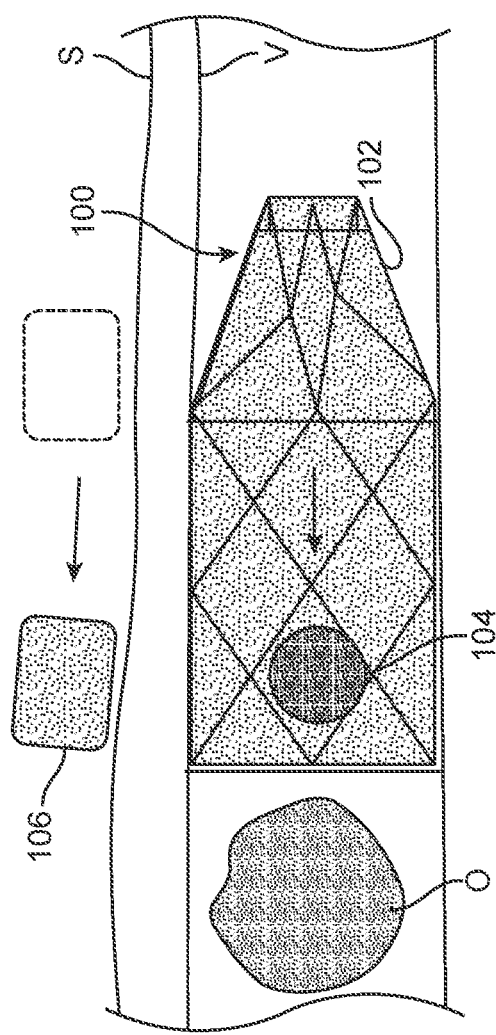
FIG. 11A
FIG. 11B

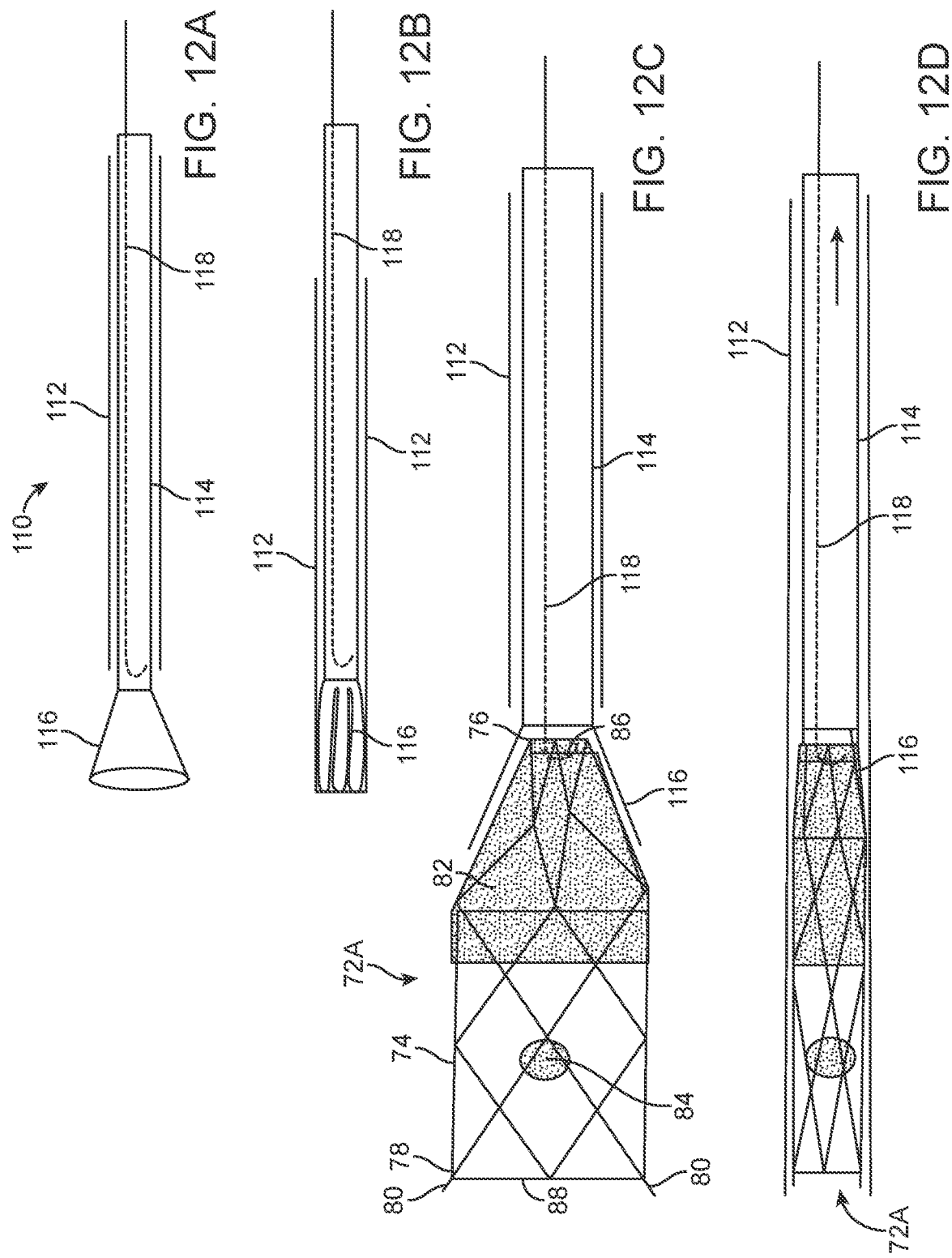

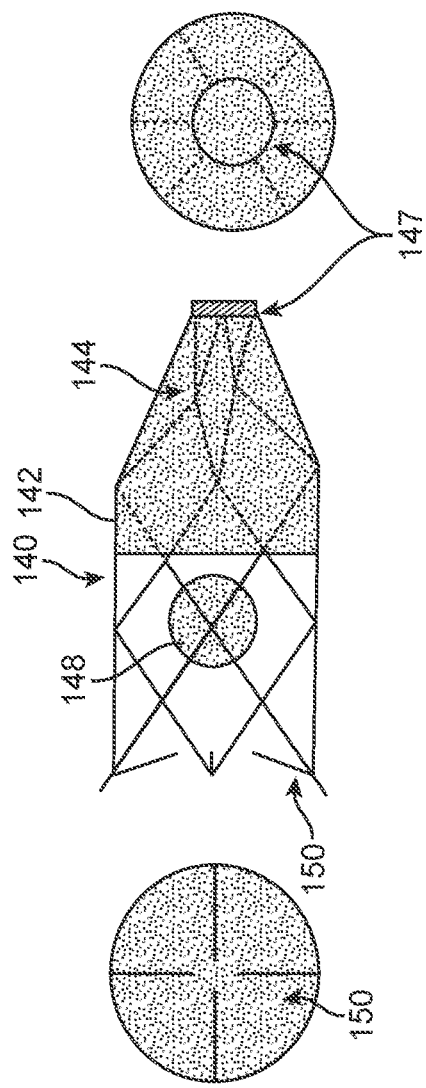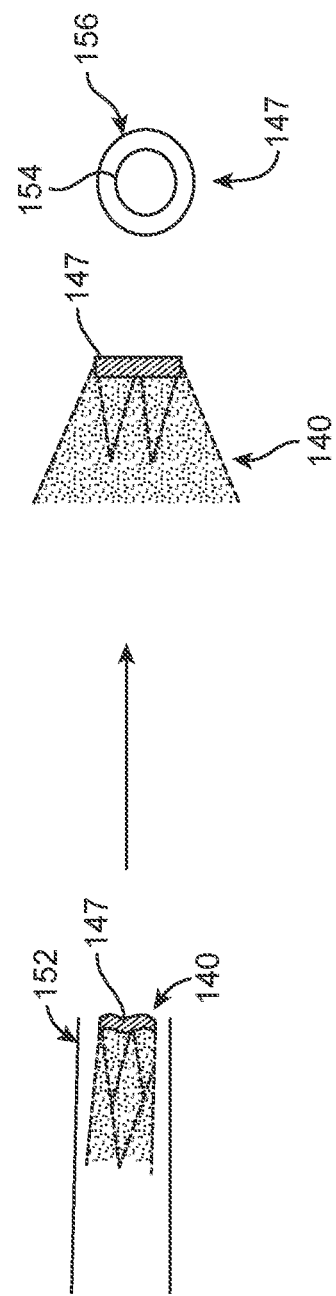
FIG. 16C
FIG. 16D

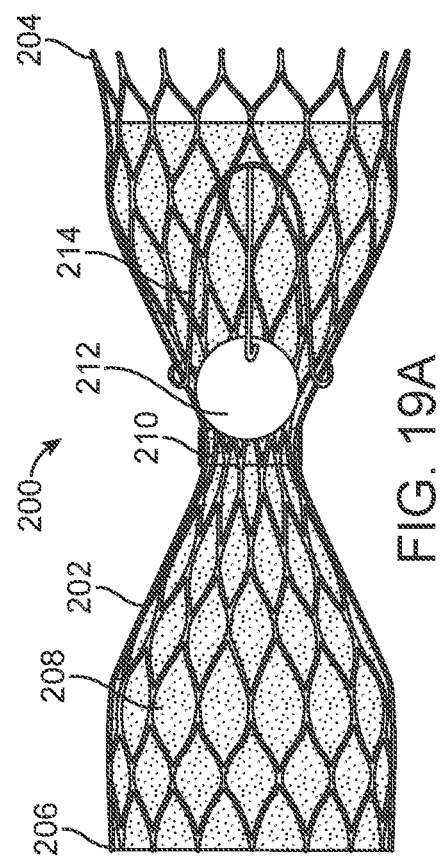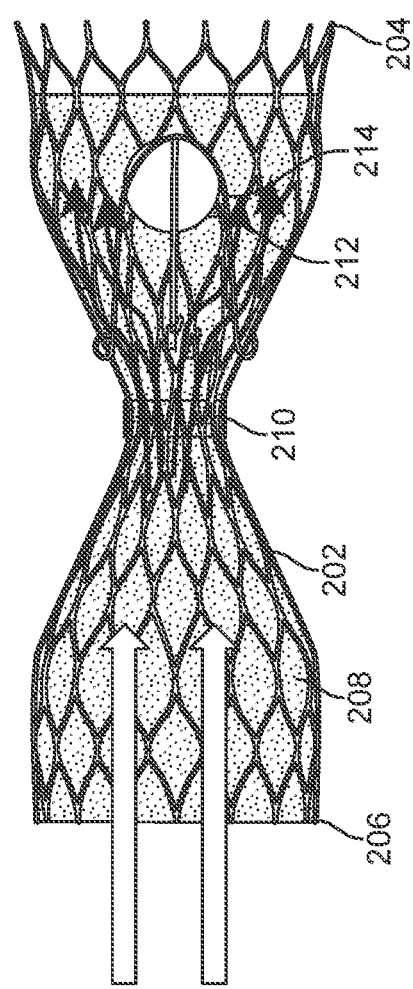

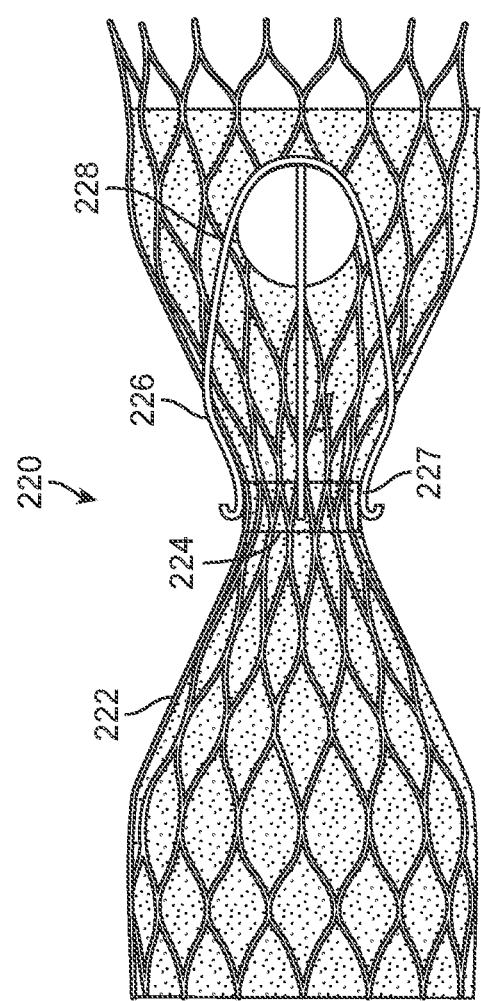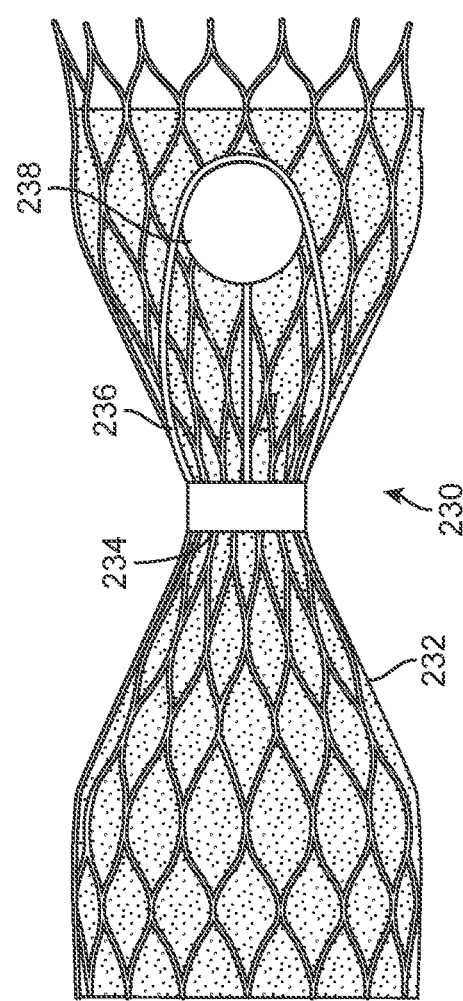

VENOUS VALVE PROSTHESIS

CROSS-REFERENCE TO RELATED APPLICATIONS

This application is a continuation of U.S. patent application Ser. No. 15/247,523, filed on Aug. 25, 2016, now U.S. Pat. No. 10,231,838, which claims priority to U.S. Provisional Application Nos. 62/209,351, filed Aug. 25, 2015, and 62/356,337, filed Jun. 29, 2016, all entitled "VENOUS VALVE PROSTHESIS." The entireties of the above applications are herein incorporated by reference for all purposes.

TECHNICAL FIELD

Embodiments described herein relate generally to the field of medical devices. More specifically, the embodiments relate to prosthetic valve implant devices and methods, for implantation within the vasculature.

BACKGROUND

Venous disease, due to incompetent venous valves, is a prevalent clinical problem. In the U.S., 20 million patients demonstrate chronic venous insufficiency, with swelling, pain, and/or ulceration of the affected extremity. An additional 74 million patients exhibit the dilation and deformity of varicose veins.

Various approaches have been advanced for addressing the clinical problem of poorly functioning venous valves. Mauch et al. (U.S. Pat. No. 7,955,346) teach a percutaneous method for creating venous valves from native vein tissue. Laufer et al. (U.S. Pat. No. 5,810,847) describes catheter placement of a clip appliance onto the cusp of a valve to restore the function of incompetent lower extremity venous valves. Multiple designs for implantable venous valves have also been described. These designs involve implantable prosthetic valves that mimic the patient's natural (autologous) valves; that is, the implants use pliable leaflet or flap valves to restore unidirectional venous flow. Examples of such implantable venous valves are described by Acosta et al. (U.S. Pat. No. 8,246,676), Shaolian et al. (U.S. Pat. No. 6,299,637), and Thompson (U.S. Pat. No. 8,377,115), for example.

In order to mimic native human peripheral venous valves, leaflet or flap valves are formed of extremely thin membrane material, to allow the valve to open properly for return flow to occur in the low pressure venous system, while still providing proper sealing and avoiding valvular insufficiency. Prosthetic membrane or flap valves are prone to failure, due to tearing from repeated opening and closing of the leaflets, permanent closure due to thrombosis and cell adhesion to the prosthetic leaflets, or leaflet inversion and incompetence over time. Currently available replacement venous valves, whether artificial or transplanted tissue valves, also often cause problems with thrombosis or clotting during long term implantation.

Therefore, it would be advantageous to have improved implantable venous valves, which would be designed to address these challenges. It would desirable, for example, to have a prosthetic venous valve that prevents and/or accommodates for the occurrence of thrombosis or cell adhesion to the valve components during chronic valve implantation.

BRIEF SUMMARY

The embodiments described herein are directed to an implantable, prosthetic venous valve that includes a ball valve mechanism to help facilitate blood flow through a vein or, alternatively, an artery or other body lumen. The embodiments generally include an anchoring mechanism, and a ball disposed within the anchoring mechanism between a valve seat and a ball retention member. The ball moves back and forth within the lumen of the anchoring mechanism, between an open position, in which blood flows through the valve, and a closed position, in which backflow of blood through the valve is prevented. In many embodiments, movement of the ball back and forth within the lumen of the anchoring mechanism acts to "self-clean" the implant, by dislodging substances (such as thrombus) attached to one or more parts of the implant. A number of different embodiments of this implantable valve device, as well as methods for delivering the device, are described herein.

In one aspect of the present disclosure, a venous valve prosthetic implant for implantation in a vein for treatment of venous disease is described. The implant may include an expandable anchoring frame having a lumen, a first end, a second end, and a middle valve portion between the first and second ends, where the middle valve portion expands to a smaller diameter than a diameter of either the first end or the second end. The implant may also include a valve seat attached to the anchoring frame nearer to the first end than to the second end, a ball retention member attached to the anchoring frame nearer to the second end that to the first end, and a ball disposed within the lumen of the anchoring frame, between the valve seat and the ball retention member. The ball moves back and forth within the middle valve portion, between a fully open position, in which the ball contacts the ball retention member to allow forward flow of blood in a downstream direction through the implant, and a fully closed position, in which the ball contacts the valve seat to prevent backflow of blood in an upstream direction through the implant.

In many embodiments, the anchoring frame may be a tubular, stent-like lattice structure, and the implant may further include a coating disposed over at least a portion of the anchoring frame. For example, the coating may be made of at least one substance, such as but not limited to polymers, hyaluronic acid, heparin and/or anticoagulant agents. Optionally, the first end and/or the second end of the anchoring frame may have a wider expandable portion that expands to a wider diameter than an immediately adjacent portion of the anchoring frame. This wider expandable portion may form multiple anti-migration tips when the anchoring frame is expanded. In some embodiments, the coating may cover an entire surface area of the anchoring frame, other than the anti-migration tips. In addition to or in place of the anti-migration tips, some embodiments may include multiple anti-migration barbs on the anchoring frame, to prevent downstream movement of the implant within the vein.

In some embodiments, the anchoring frame may be self-expandable from a collapsed configuration, for delivery through a delivery catheter, to an expanded configuration upon release from the delivery catheter. Alternatively, the anchoring frame may be balloon-expandable. In some embodiments, portions of the anchoring frame near the first and second ends are sized to dilate the vein when the implant is implanted in the vein. Additionally, in some embodiments, the middle valve portion of the anchoring frame is also sized to dilate the vein when the implant is implanted in the vein. The middle valve portion may have any suitable diameter, length and shape. In some embodiments, for example, the middle valve portion may have a substantially straight tubular shape. Alternatively, the middle valve portion may have an hourglass shape.

The valve seat, in some embodiments, may take the form of an expandable and collapsible ring attached to at least one of an outer surface of the anchoring frame or an inner surface of the anchoring frame. The ball retention member, in some embodiments, may take the form of at least one suture member extending across the lumen of the anchoring frame. Alternatively, the ball retention member may be at least one U-shaped member attached to at least one of an outer surface of the anchoring frame, an inner surface of the anchoring frame, or the valve seat and extending across the lumen of the anchoring frame.

The ball itself may have any of a number of different sizes, shapes and materials. For example, in some embodiments, the ball may include a shell and a core. The shell and core may be of the same material, or alternatively the shell may be made of a first material, and the core may be made of a second material. In some embodiments, the shell may include at least one aperture, and the core may include at least one therapeutic substance configured to pass through the aperture. In some embodiments, the ball may be collapsible. The core may include a substance that is injected through the shell. In some embodiments, the core may be a magnetic material.

In a number of embodiments, the ball may be sized, relative to the anchoring member, so that the valve works optimally and also so that the balls movement through the anchoring member acts to self-clean the implant. For example, in some embodiments, a distance between the valve seat and the ball retention member is between two times and four times greater than the ball diameter. In some embodiments, the ball diameter is sized such that the ball contacts an inner surface of the middle valve portion as the ball travels back and forth between the valve seat and the ball retention member, so that contact between the ball and the middle valve portion is configured to dislodge a substance attached to at least one of the inner surface of the middle valve portion, the valve seat, the ball, or the ball retention member. In some embodiments, the ball may have a density that is equal to, approximately equal to, or slightly greater than the average density of blood. For example, in some embodiments the ball may have a density of between about 1.06 grams per cubic centimeter and about 2.5 grams per cubic centimeter. In some embodiments, the ball may also include at least one surface feature configured to facilitate flow of blood around the ball, such as but not limited to dimples, slits or grooves. In some embodiments, the valve seat and the middle valve portion of the anchoring frame are compressible from outside of the implant to facilitate dislodging a substance attached to the implant. In some embodiments, the implant may further include an inner tubular ball valve frame disposed inside the middle valve portion of the anchoring frame, such that the valve seat and the ball retention member are disposed at opposite ends of the ball valve frame.

In another aspect of the present disclosure, a method for treating a vein may involve advancing an implant delivery catheter into the vein, advancing a venous valve prosthesis implant out of a distal end of the delivery device and into the vein, thus causing the implant to expand and anchor itself to an inner wall of the vein, and removing the delivery catheter from the vein, leaving the implant in place within the vein to help facilitate blood flow through the vein. In various embodiments, the venous valve prosthesis implant may have any of the characteristics or features described immediately above or in the detailed description that follows below.

In some embodiments, the method may further involve dilating the vein with at least a first portion of the anchoring frame adjacent the first end and a second portion of the anchoring frame adjacent the second end. Optionally, the method may further include dilating the vein with the middle valve portion of the anchoring frame. The method may also include dislodging a substance attached to an inner surface of the middle valve portion, the valve seat, the ball, and/or the ball retention member of the anchoring frame, and thus self-cleaning the anchoring member, by providing the ball with a diameter configured so that the ball contacts the inner surface of the middle valve portion as it moves back and forth between the valve seat and the ball retention member.

The method may also optionally include applying external compression to the implant to expel an obstruction out of the implant. In some embodiments, the ball may include a magnetic material, and the method may further involve moving a magnet outside of the implant to cause the ball to move back and forth within the middle valve portion to expel an obstruction out of the implant. The method may also include removing the ball and/or the valve seat from the implant, while leaving the implant in the vein. The ball and/or the valve seat may optionally be replaced with a new, cleaned or repaired ball and/or valve seat, while still leaving the implant in place within the vein.

In another aspect of the present disclosure, a venous valve prosthetic implant system for implantation in a vein for treatment of venous disease may include a prosthetic implant, as described above, and an implant delivery catheter configured to house and deliver the prosthetic implant into the vein. In various embodiments, the venous valve prosthesis implant may have any of the characteristics or features described immediately above or in the detailed description that follows below. In some embodiments, where the implant is self-expanding, the implant delivery catheter may include a tubular catheter body and a pusher member disposed inside the tubular catheter body and configured to slide through the tubular catheter body to push the implant out of a distal end of the tubular catheter body.

These and other aspects and embodiments are described in greater detail below, in the detailed description and attached drawing figures.

BRIEF DESCRIPTION OF THE DRAWINGS

FIGS. 1A and 1B are perspective views of a prosthetic venous valve implant, illustrating an optional membrane in FIG. 1B, according to one embodiment;

FIGS. 8A and 8B are side, cross-sectional views of a blood vessel and a prosthetic venous valve implant, according to an alternative embodiment;

FIGS. 10A and 10B are side views of a prosthetic venous valve implant, illustrating a method for squeezing an obstruction such as a thrombus out of the implant, according to one embodiment;

FIGS. 11A and 11B are side views of a prosthetic venous valve implant, illustrating a method for ejecting an obstruction such as a thrombus out of the implant using a magnet, according to one embodiment;

FIGS. 12A-12D are side views of a venous valve and a removal system, illustrating a method for removing an implanted valve, according to one embodiment;

FIGS. 16C and 16D are side and end views of the prosthetic venous valve implant of FIGS. 16A and 16B, but with an alternative embodiment of a valve seat, according to another alternative embodiment;

FIGS. 19A and 19B are side, cross-sectional views of a venous valve implant with a diverging middle portion design, according to an alternative embodiment;

FIG. 20 is a side, cross-sectional view of a venous valve implant with a ball retention cage attached to an outside of an anchoring member, according to one embodiment;

FIG. 21 is a side, cross-sectional view of a venous valve implant with a ball retention cage attached to an inside of a valve seat, according to an alternative embodiment;

DETAILED DESCRIPTION

Figure 2:
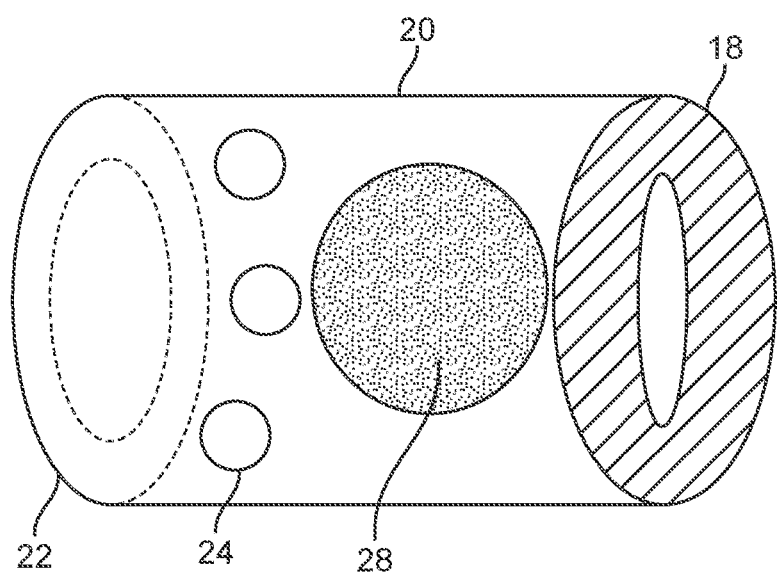
FIG. 2 is a perspective view of an inner, ball valve portion of the prosthetic venous valve implant of FIGS. 1A and 1B.

In general, the embodiments described herein provide an implantable valve device for treating venous insufficiency. In various embodiments, the implantable valves described herein may be used in veins or alternatively in arteries or other lumens of a human or animal body, such as the urinary tract, the gastrointestinal tract, the bile duct, or the like. Thus, although the following description focuses on the use of implantable valve embodiments in veins to treat venous insufficiency and related conditions, this disclosure is not limited in scope to such applications.

The embodiments described in detail below generally include an anchoring member, a ball housed within the lumen (or "inside") of the anchoring member, and at least two stop features attached to, or formed by, the anchoring member to retain the ball within the lumen of anchoring structure. The anchoring member is typically expandable—either self-expanding or expanded by another device—so that it can be delivered into a vein or other blood vessel within a catheter, sheath or other similar delivery device and then released from the delivery device for expansion. When expanded, the anchoring member attaches to the inner wall of the vein or other vessel via outwardly directed expansive force and/or one or more attachment features of the anchoring member. In some cases all or one or more portions of the anchoring member may expand to a diameter that is sufficient to dilate the vein or other vessel in which it is implanted. Once the valve implant device is delivered, the ball is free to move back and forth within the anchoring member, between the two stop features, to transition the valve implant from an open position, in which blood is free to flow through the implant in its forward-flowing direction, to a closed position, in which blood is prevented from back-flowing through the implant. In some embodiments, for example, one of the stop features is referred to as a "valve seat," and the stop feature is referred to as a "retention member." The embodiments described herein generally provide for a low-profile, easily delivered and effective prosthetic valve, which may be used to ameliorate venous valve insufficiency and/or other conditions of the veins or other blood vessels in patients.

Referring now to FIGS. 1A and 1B, in one embodiment, a prosthetic venous valve implant 10 may include an anchoring member 12 (or "anchor frame"), such as a self-expanding, stent-like frame, for anchoring the implant 10 within a vein. The anchoring member 12 may have a first end 14 (sometimes referred to herein as an "upstream end"), a second end 16 (sometimes referred to herein as a "downstream end"), and a middle valve portion 13. Although not labeled FIGS. 1A and 1B, portions of the anchoring member 12 that lie between the first end 14 and the middle valve portion 13 and between the second end 16 and the middle valve portion 13 may be referred to as an "upstream portion" and a "downstream portion," respectively, of the anchoring member 12. In many embodiments, there is no clear delineation or demarcation between the various portions of the anchoring member 12, and these descriptive terms are used for explanatory purposes only and should not be interpreted as limiting the scope of the invention. Optionally, as illustrated in FIG. 1B, all or a portion of the anchoring member 12 may be coated or otherwise covered with a membrane 26, to help direct blood flow through the implant 10 and prevent blood from flowing through the wall of the anchoring member 12 in the coated portion. In some embodiments, the membrane 26 may be made of or coated with an anticoagulant substance. In general, the anchoring member 12 is configured to anchor the valve implant 10 to the luminal surface of the vein.

The venous valve implant 10 may also include a tubular frame 20, which is housed within the anchoring member 12, and a ball 28 housed within the tubular frame 20. Attached to, or integrally formed with, the tubular frame 20 are a valve seat 18, a retention member 22, and multiple through-holes 24, through which blood is free to exit the tubular frame 20. In some embodiments, the tubular frame 20, valve seat 18, retention member 22 and ball 28 may be referred to as the "valve portion" of the implant device 10, which is housed within the anchoring member 12.

In alternative embodiments, which will be described further below, the prosthetic venous valve implant may include fewer parts than in the valve implant 10 of FIGS. 1A and 1B. For example, one embodiment may simply include an outer anchoring device, such as a self-expanding stent, along with a distal retention feature, such as crossing suture, and a ball disposed with the lumen of the anchoring device. Other embodiments may include additional components or features, such as retaining barbs on an anchoring member. A number of these alternative embodiments and features are described in greater detail below.

Referring now to FIG. 2, one embodiment of the valve portion of the prosthetic venous valve implant 10 of FIGS. 1A and 1B is illustrated in further detail. In this embodiment, as mentioned above, the valve portion includes the ball 28, tubular frame 20, valve seat 18 at an upstream (or "inlet") end of the tubular frame 20, and retention member 22 at the opposite, downstream (or "outlet") end of the tubular frame 20. The tubular frame 20 may optionally include one or more through holes 24 leading from the inside to the outside of the tubular frame 20. The ball 28 may be rigid or flexible, solid or hollow, metal (such as stainless steel), ferromagnetic, or polymeric (such as PTFE). A flexible/collapsible ball design can allow the device to be packed into small sheath sizes. The density of the ball 28, in some embodiments, may be equal to, approximately equal to, or slightly greater than the average density of venous blood (or arterial blood in other embodiments), so the valve functions with both a low opening pressure and a low closing pressure. For example, in some embodiments, the ball 28 may have a density of between about 1.06 grams per cubic centimeter (approximately the density of blood) and about 2.5 grams per cubic centimeter, or more specifically between 1.2 and 2.5 grams per cubic centimeter. In alternative embodiments, the density of the ball 28 may fall outside these ranges, such as between about 1.00 grams per cubic centimeter and just below about 1.06 grams per cubic centimeter, or slightly above 2.5 grams per cubic centimeter. The ball 28 may be constructed out of PTFE (polytetrafluoroethylene), silicone rubber, silastic rubber, silicone, stainless steel, Teflon, or other material. Optionally, an anti-coagulant agent, such as heparin, or another coating, such as hyaluronic acid, may be bonded to the surface of the ball 28. The valve seat may be formed of toroidal elastomer, silicone rubber, or other material.

Figure 22A:
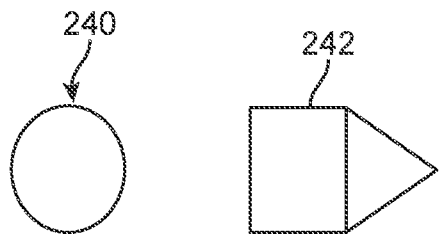
FIGS. 22A-22C are front and side views of three different embodiments of a ball for use in a prosthetic venous valve implant.
Figure 22B:
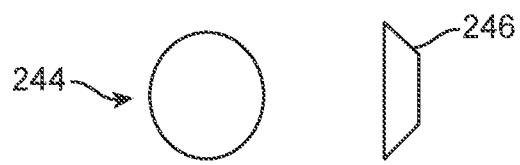
Figure 22C:
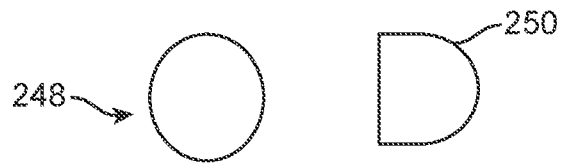

In various alternative embodiments, the ball 28 may have any suitable shape, size, surface feature(s) or the like. In its simplest form, for example, the ball 28 may be spherical and solid. Alternatively, and with reference now to FIGS. 22A-22C, a ball incorporated into a prosthetic valve implant of the present disclosure may have any of a number of alternative shapes, such as ovoid, oblong, asymmetrical, etc. As illustrated in FIG. 22A, a ball 240 according to one embodiment may have a shape 242, when viewed from the side, of a cylinder with a pointed end. As illustrated in FIG. 22B, a ball 244 according to another embodiment may have a shape 246, when viewed from the side, of rhombus. As illustrated in FIG. 22C, a ball 248 according to yet another embodiment may have a shape 250, when viewed from the side, of a cylinder with a rounded end. Any other shape may be used, according to alternative embodiments. In some embodiments, the ball 28 may have an outer shell and an inner core, and these two parts may be made of different substances. In some embodiments, the inner core may be made of a liquid substance, and in some embodiments the liquid may be injected through the outer shell to fill the core. The substance may be an anticoagulant or other drug or therapeutic substance and may leak out of one or more holes in the shell in some embodiments. The ball 28 may also have surface features, such as dimples, grooves, indents, pockets or the like. In embodiments, for example, surface features may facilitate the flow of blood around the ball 28.

Returning to FIG. 2, the retention member 22 (or "ball-retaining cap") may be a circular constriction, a crossing of suture, an arch of possibly crossing material, such as stainless steel, titanium, Nitinol, stellite, silicone, or other blood friendly material, or formed via other such mechanism, in various embodiments. The valve seat 18 may be either rigid (e.g., stainless steel or polycarbonate) or elastomeric (e.g., silicone rubber). The tubular frame 20 may be constructed of stainless steel, a rigid plastic material such as polycarbonate, a flexible material such as silicone, or any other suitable material. Multiple through holes 24 may be incorporated into the tubular frame 20, to ensure unobstructed retrograde venous return flow. The tubular frame 20 may have an outer diameter between 1 mm and 30 mm, and a length between 1 mm and 100 mm. More specifically, in some embodiments, the tubular frame 20 may have an outer diameter between 2 mm and 20 mm, and a length between 5 mm and 15 mm. The ball 28 may have a diameter of between 0.5 mm and 30 mm. More specifically, in some embodiments the ball 28 may have a diameter between 1 mm and 8 mm.

Figure 3A:
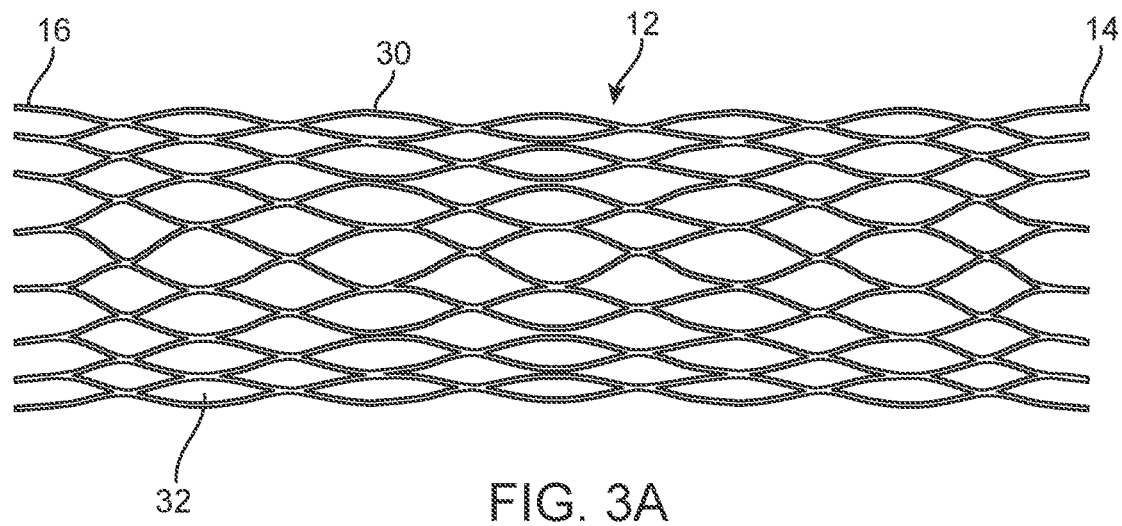
FIGS. 3A and 3B are perspective views of an anchoring member self-expanding frame of the prosthetic venous valve implant of FIGS. 1A and 1B, in pre-heat-treated and heat-treated configurations, respectively, according to one embodiment.
Figure 3B:
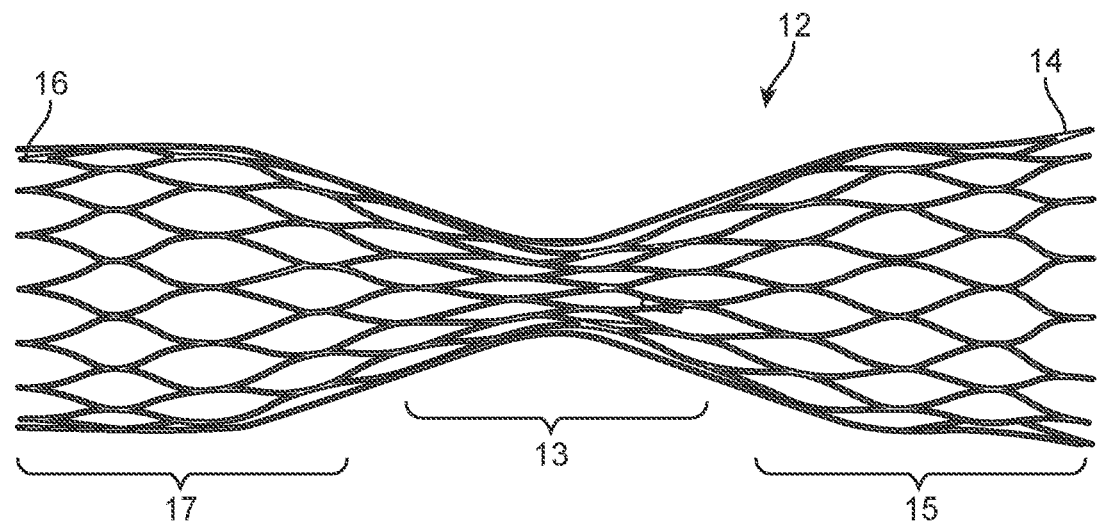

With reference now to FIGS. 3A and 3B, the anchoring member 12 is illustrated in further detail. In various embodiments, the anchoring member 12 may be formed as a stent-like lattice structure 30, with open portions 32 within the lattice. The anchoring member 12 may be either self-expanding or expandable, such as with a balloon catheter. In some embodiments, all or a portion of the self-expanding frame may be coated, to render it impervious to blood flow. The anchoring member 12 may be a frame constructed of an engineered polymer (i.e., PEEK, Polypropylene, PTFE, etc.), stainless steel, or a superelastic metal, such as Nitinol. A Nitinol tube may be laser cut in a lattice pattern 30. As illustrated in FIG. 3B, in some embodiments, the middle valve portion 13 of the anchoring member 12 may either not expand or may expand less than (to a smaller diameter than) an upstream portion 15 and a downstream portion 17 of the anchoring member 12. The upstream portion 15 and downstream portion 17 may be expanded, for example, to between 1 mm and 30 mm, and the middle valve portion 13 may be between 1 mm and 30 mm. More specifically, some embodiments may have an upstream portion 15 and a downstream portion 17 that expand to between 10 mm and 20 mm, and a middle valve portion 13 that may be between 2 mm and 10 mm. The length of the anchoring member 12 may be between 1 mm and 200 mm, with some embodiments between 20 mm to 40 mm. The first end 14 and the second end 16 of the anchoring member 12 may have multiple apices, which, when expanded, anchor the anchoring member 12 to the inner wall of the vein. The anchoring member 12 may be heated above its transition temperature and quenched, to place it in its austenitic, self-expanding state.

Figure 4A:
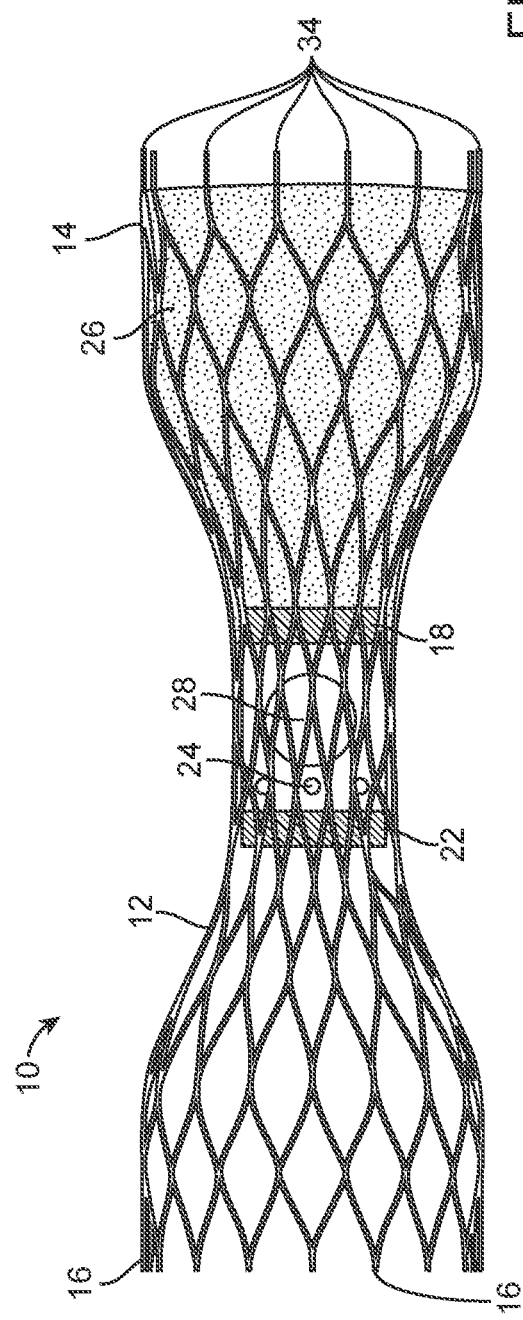
FIG. 4A is a perspective views of the prosthetic venous valve implant of FIG. 1B, with an added optional feature of barbs, according to one embodiment.
Figure 4B:
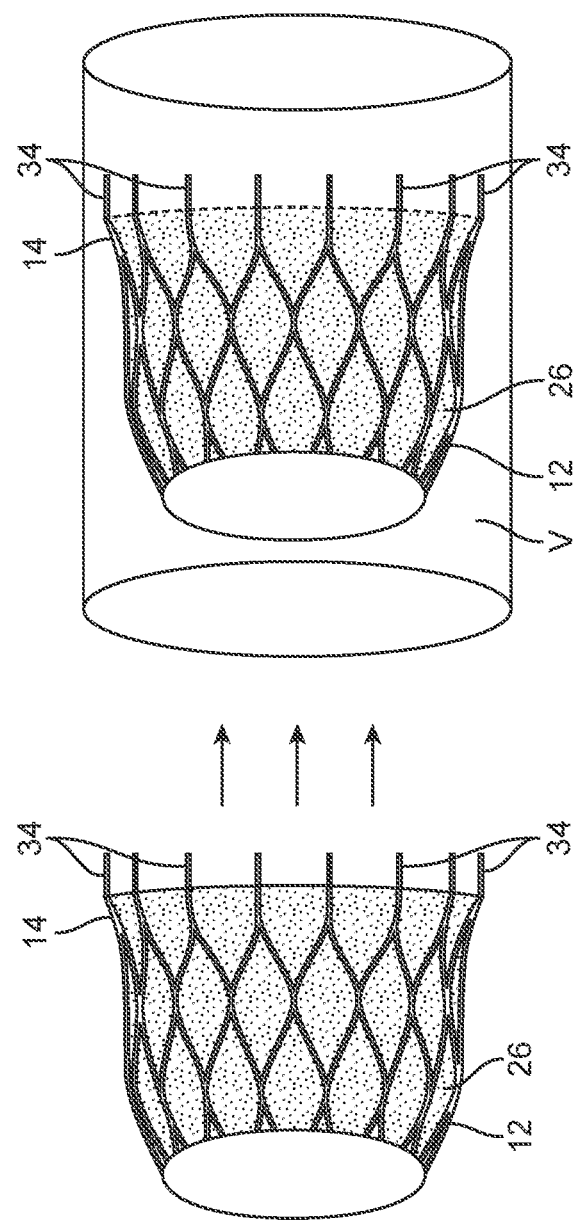
FIG. 4B is a perspective view of the downstream portion of the prosthetic venous valve implant of FIG. 4A, illustrating sealing of the implant to a wall of a vein, according to one embodiment.

Referring now to FIGS. 4A and 4B, in some embodiments, the tubular frame 20 may be attached to the middle valve portion 20 of the anchoring member 12, and the open areas 32 of the lattice 30 may be closed off via the membrane 26, which may be a thin layer of silicone rubber or a covering membrane such as PET (polyethylene teraphthalate), PTFE, Nylon, hyaluronic acid or other material. In some embodiments, the membrane 26 may have anticoagulant properties and may thus be referred to herein as an "anticoagulant membrane," even though the anticoagulant properties are not required. The membrane 26 may also be referred to in this application as a "hemostatic membrane," because it prevents or helps prevent blood from flowing through the openings in the wall of the anchoring member 12. The membrane 26 may cover the inlet and/or outlet sections of the anchoring member 12 and may thus, when the anchoring member 12 is expanded, form a seal against the inner vein wall, to prevent leakage around the outside of the anchoring member 12. Sealing may also be facilitated by adding short barbs 34 onto the apices first end 14 (or "inlet" or "upstream" end). In various alternative embodiments, barbs 34 may be included on the second end 16, on both the first and second ends 14, 16, on the middle valve portion 13, or on any combination thereof. FIG. 4B illustrates insertion of the inlet/upstream section of the valve implant 10 into a vein V. The first end 14 of the implant 10, with the membrane 26, may form a circumferential linear seal against the inner surface of the vein V, facilitated by the barbs 34 protruding into the vein wall. The edge of the membrane 26 may also be thickened with respect to the remainder of the membrane 26, to enhance its sealing capability.

Figure 5:
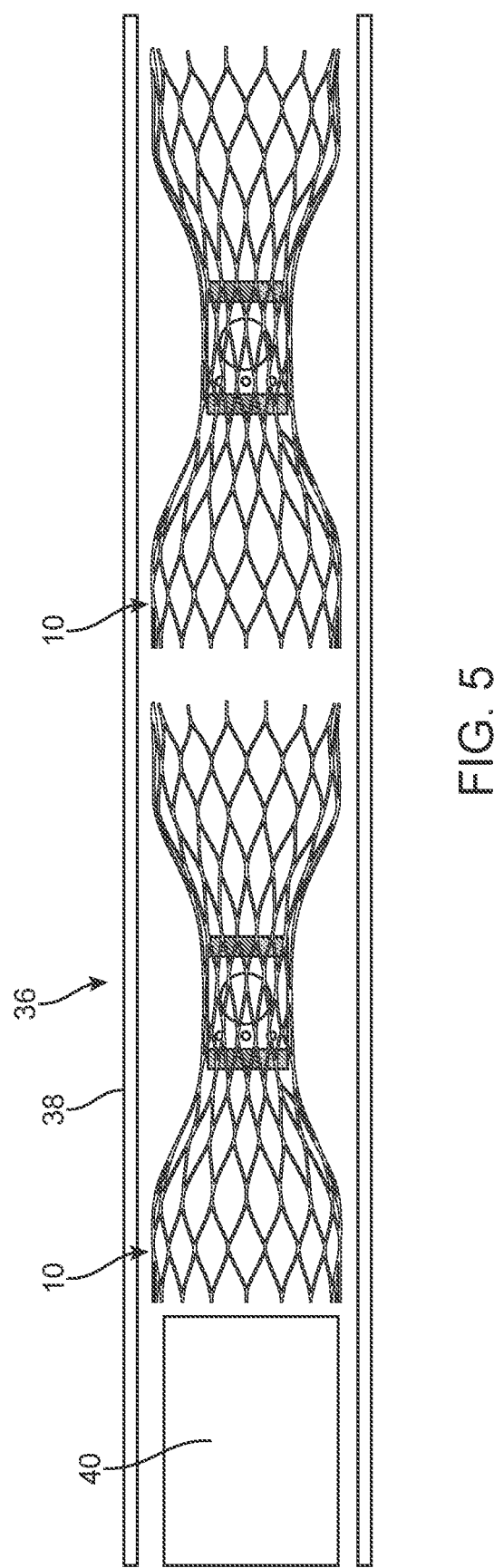
FIG. 5 is a side, cross-sectional view of a catheter delivery device for delivering one or more prosthetic venous valve implants, according to one embodiment.
Figure 6A:
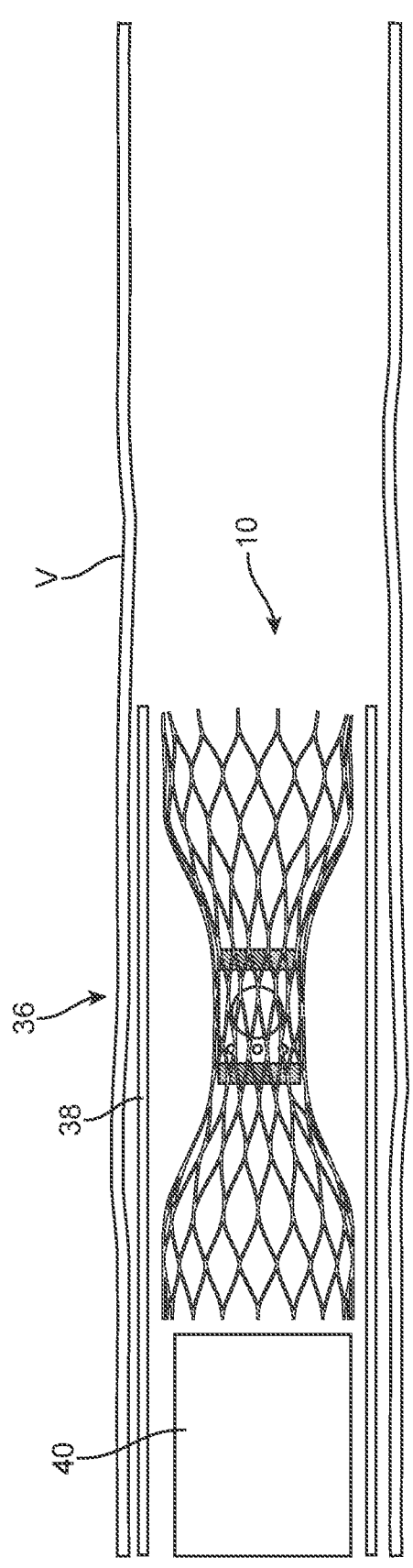
FIGS. 6A and 6B are side, cross-sectional views of a blood vessel and a prosthetic venous valve implant, illustrating a method for delivering the implant via a catheter delivery device, according to one embodiment.
Figure 6B:
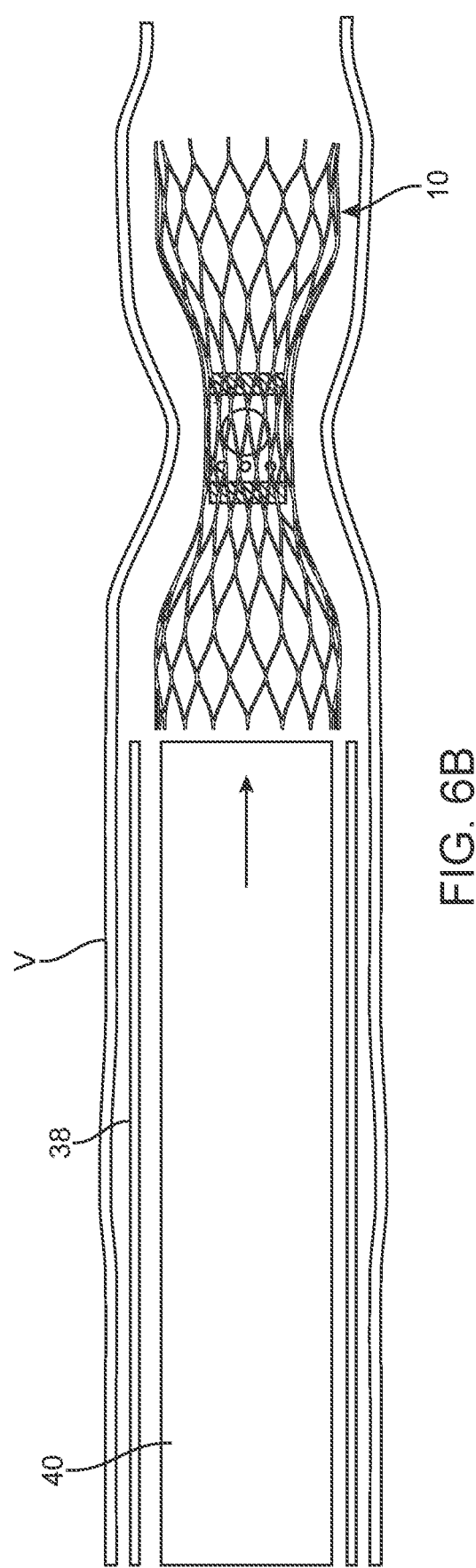

Referring now to FIGS. 5, 6A and 6B, the venous valve prosthesis 10 may be delivered into a vein via an intravascular delivery device 36 that includes a flexible intravascular catheter 38 and a flexible pusher 40 (or "plunger") inside the catheter 38. The expanded portions of the anchoring member 12 may be compressed, and multiple prostheses 10 may be inserted into the lumen of the delivery catheter 38, as shown in FIG. 5. The pusher 40 abuts the series of prostheses 10, and the proximal end of the pusher 40 extends out of the proximal end of the catheter 38. The valve prostheses 10 may be delivered serially, at desired intervals within the vein. FIGS. 6A and 6B illustrate one embodiment of a method for delivering the prosthesis 10 into a vein V. The proximal and distal portions of the prosthesis 10 may expand within the lumen of the vein V, anchoring the prosthetic valve 10 against migration in either direction following placement.

A more detailed description of the method embodiment illustrated in FIGS. 6A and 6B for delivering the venous valve prosthesis 10 is as follows: The catheter 38 containing multiple compressed venous valve prostheses 10 is advanced through the vein V under fluoroscopic or ultrasonic control to the desired site of implantation. The distal-most venous valve prosthesis 10 is ejected from the distal end of the catheter by advancing the plunger 40 while holding the catheter 38 stationary or holding the plunger 40 stationary and retracting the delivery catheter 38 relative to the plunger 40. Upon ejection from the delivery catheter 38, the venous valve prosthesis 10 may distend the vein V past its native resting diameter. Distention of the vein V at the site of implantation can increase the ability of the prosthetic valve 10 to anchor itself without the potential for migration, as well as to maximize the cross-sectional flow area through the valve device 10 to provide low flow resistance. In some embodiments, the apices of the self-expanding anchoring member 12 may protrude into the vein wall and/or be tilted out toward the vein wall to enhance anchoring.

One advantage of the self-expanding venous valve prosthesis 10 is its sealing mechanism, which incorporates a significantly more substantial valve structure—the moveable ball 28 that seats onto the ring of the valve seat 18. Other advantages include the self-expanding frame/anchoring member 12 that distends the vein wall upon deployment, to prevent valve migration, maximize flow-through area, and minimize sheath size for introducing the device 10 and the impermeable covering 26. Use of a ball valve instead of super-thin membranes or leaflets imparts longevity to the implant 10. A venous valve prosthesis formed of thin membranes or leaflets is prone to early failure, due to fatigue, leaflet disruption, and thrombus and cellular adhesion to the leaflets. Due to the larger size and greater mass of the ball 28, compared to thin leaflets, and due to the greater excursion of a rolling ball 28 upon opening and closing of the valve, a ball valve will avoid at least some of the sealing and fatigue problems encountered with thin membrane and leaflet valves. Another advantage of the venous valve implant device 10 is that it is able to clean itself, at least in part, as the ball 28 rolls back and forth and thus cleans off the inner surface of the tubular frame 20, the anchoring member 12, the valve seat 18 and/or the retention member 22. To provide adequate excursion of the rolling ball 28 for the purpose of self-cleaning the device 10, the distance between the valve seat 18 and the retention member 22 may be about two to four times greater than the diameter of the ball 28. In alternative embodiments, this distance may be longer or shorter, such as about 1.5 to about five times greater than the diameter of the ball 28, for example. As the ball 28 moves back and forth, it rubs against the inside of the ball valve frame 20, dislodging potential adherent cells and thrombus. In embodiments described further below that do not include a tubular frame 20, the ball 28 may instead clean an inner surface of the anchoring member 12.

Figure 7A:
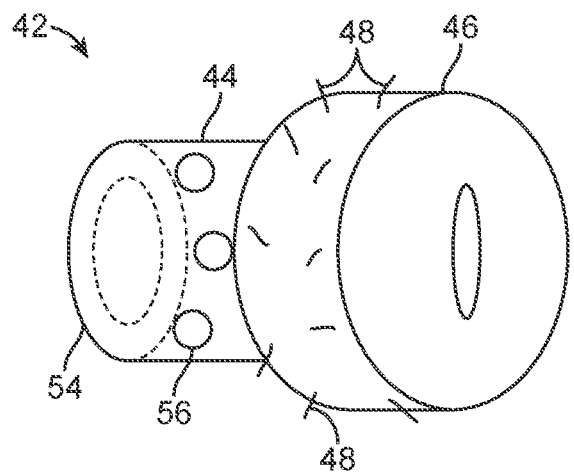
FIGS. 7A and 7B are perspective and partial cross-section views, respectively, of a prosthetic venous valve implant with a foam anchoring member, according to an alternative embodiment.
Figure 7B:
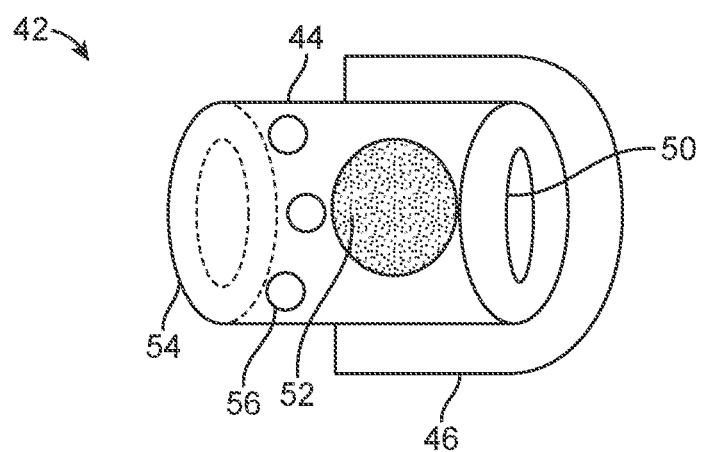

Referring now to FIGS. 7A and 7B, an alternative venous valve prosthesis implant 42 may include a tubular frame 44, valve seat 50, retention member 54, through holes 56 and ball 52, all of which are the same as, or substantial to, the embodiments described above. In this embodiment, however, a different anchoring member is employed, in the form of an expanding foam cuff 46 surrounding at least a portion of the outer surface of the tubular frame 44. The foam cuff 46 may be closed cell polyurethane or silicone foam, for example, which may be compressed during insertion into the delivery catheter and which self-expands upon delivery into the vein. The expanding foam 46 anchors the prosthetic valve device 42 and seals against blood flow between the ball valve portion and the vein luminal wall. Short bristles 48 of spring metal wire or polymer, such as nylon, may be embedded in the expanding foam anchor 46, to increase the grip of the anchor 46 with the vein wall.

With reference now to FIGS. 8A and 8B, in another alternative embodiment, a venous valve prosthesis implant 60 may incorporate a pre-formed, self-expanding, stent-like anchoring member 62, in which the first end 64 (or "upstream" or "distal" end) and the second end 66 (or "downstream" or "proximal" end) conform to or expand the diameter of the vein, and the center portion 63 (or "middle valve portion") further expands (i.e., to a greater diameter than the other two portions), to maximize flow while retaining the ball 68. The implant 60 may also include one or more retention members 70 attached to the anchoring member 62. The ball 68 seals at the inlet end, to prevent retrograde flow (FIG. 8A), and is captive at the outlet end with the retention member 70, while allowing blood to flow past (FIG. 8B). Generally, the embodiment of the venous valve implant 60 shown here has an anchoring member 62 that is the reverse of the anchoring members described above, in that the ends of the anchoring member 62 expand to a smaller diameter than the expanded diameter of the middle valve portion 63. In such embodiments, one or both ends of the anchoring member 62 may act as stops for the ball 68. Otherwise, the ball 68, retention member 70, a valve seat, and anchor features, such as a coating or anti-migration barbs, if used, may all be the same as the embodiments described elsewhere in this application. Similarly, the method of deployment and removal, as discussed in-depth elsewhere in this application, may be used with this embodiment.

As mentioned above, one of the challenges that occurs with prosthetic venous valves is thrombosis (or "clot") formation. In an effort to address this concern, several embodiments of venous valve implants are described in further detail immediately below. One embodiment is an implantable valve with cleaning properties, either external to the patient, or intrinsic. Another embodiment is a venous valve prosthesis that may be removed in its entirety and replaced upon thrombotic occlusion. In another embodiment, a valve portion of the implant may be replaceable, if it becomes non-functional, while the anchor portion of the implant remains in position in the vein.

Figure 9C:
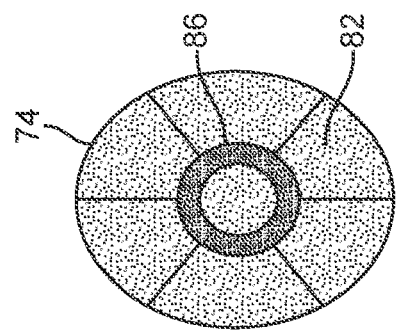
FIGS. 9A-9C are side, rear and front views, respectively, is a side view of a prosthetic venous valve implant, according to another alternative embodiment.
Figure 9B:
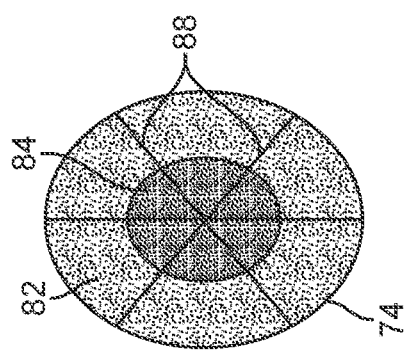
Figure 9A:
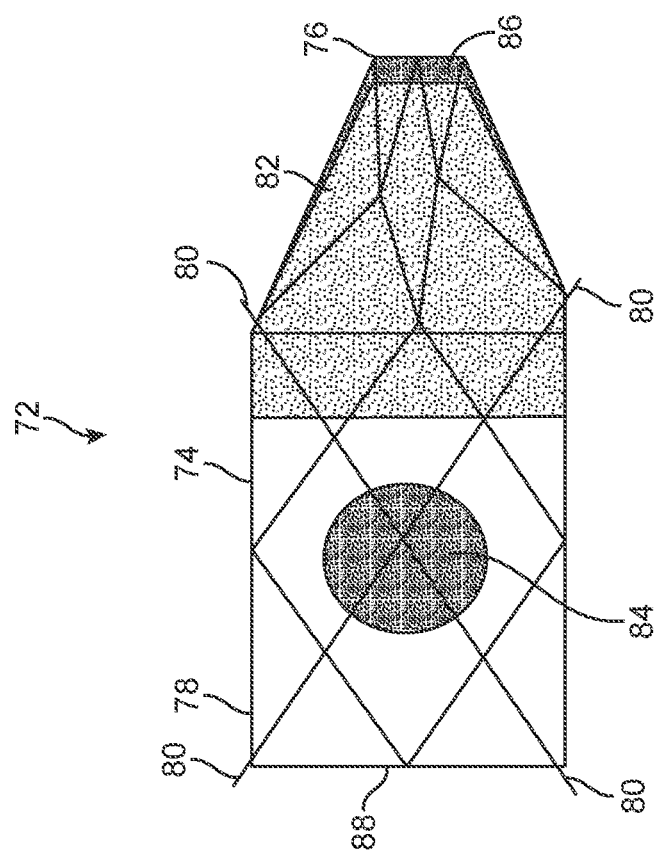

FIGS. 9A-9C are side, rear and front views, respectively, of another alternative embodiment of a prosthetic venous valve implant 72, which may be cleared of thrombus that forms inside the implant 72. In this embodiment, the prosthesis 72 includes a superelastic metal frame anchoring member 74 (e.g., nickel-titanium alloy or Nitinol), which tapers down at a first end 76 to accommodate the attachment of a flexible valve seat 86. The valve seat 86 may be formed of silicone rubber, or a flexible polymer, such as Viton, for example, and it may be insert-molded into (or attached to) the tapered first end 76 of the Nitinol frame 74. The anchoring member 74 may contain multiple barb extensions 80, for example at the second end 78 and along the length of the anchoring member 74, which extend into the vein wall and anchor the prosthesis 72 against implant migration. A flexible thin membrane 72 encloses the tapered portion of the anchoring member 74, extending up to at least partially cover the major diameter of the expanded portion of the anchoring member 74. The thin membrane 82 may be composed of silicone rubber or a polymer, such as but not limited to polytetrafluoroethylene (PTFE), nylon, or similar material. The membrane 82 may be fluid impermeable, and when the anchoring member 74 is expanded, the membrane 82 may seal the anchoring member 74 against the inner surface of the vein wall. The ball 84, valve seat, and retainer may have any characteristics of the embodiments described elsewhere in this application. In various embodiments, some or all of the surfaces of the valve components may be coated with an anti-thrombogenic agent, such as heparin sodium, or other material such as hyaluronic acid.

FIG. 9B, a rear view of the prosthetic venous valve 72, illustrates the retention member 88, which in this embodiment includes multiple crossing members disposed across the lumen of the anchoring member 74. In one embodiment, for example, the retention member 88 is multiple, crossing sutures. FIG. 9C is a front view of the prosthetic valve implant 72, showing the valve seat 86.

Referring now to FIGS. 10A and 10B, another embodiment of a prosthetic venous valve implant 90 is illustrated, similar to the embodiment shown in FIGS. 9A-9C, but with a coating membrane 96 extending over the entire surface of the anchoring member 92. FIG. 10B illustrates the flexibility of the anchoring member 92, sealing membrane 96, and valve seat 98, which allows external compression and massage to be performed in the event of obstruction O (or "thrombus") formation inside the implant 90. FIG. 10A shows the obstruction O in the implant 90, and FIG. 10B illustrates a method for squeezing the obstruction O out of the implant 90, using compression applied from outside the patient, on the skin S. The external compression and massage deforms the anchoring member 92 and expels the clot, thrombus or other obstruction O, without dislodging the prosthesis 90 from the vein V. Thrombus and other material that typically would cause obstruction of a prosthetic venous valve implant 90 is usually relatively soft and/or friable, so that when it is pushed out of the end of the implant 90, through the retention member(s), it will typically either cut, crumble or break apart, or alternatively it will simply pass through an opening in the retention member(s). Upon clearing of internal clot from the prosthesis 90, valve function is restored. This same approach may be used with many of the alternative valve implant designs described herein.

Referring to FIGS. 11A and 11B, in another embodiment, a venous valve prosthesis 100 with external cleaning capability may include a ball 104 that is ferromagnetic, so that the ball 104 responds to the translation of an externally placed magnet 106. In one embodiment, for example, the ball 104 may include a solid or hollow ferromagnetic metal shell, with a thin outer polymer coat of PTFE or similar material. The polymer coat prevents corrosion of the inner metal shell and provides a smooth surface that discourages cell and thrombus adhesion. Heparin coating of the prosthesis components may also be added, to avoid thrombus formation in the implant 100. If an obstruction O (thrombus, etc.) does occur, a powerful rare earth Neodymium magnet 106 may be placed on the skin S overlying the vein V and the implant 100, and repeated movement of the magnet 106 back and forth over the prosthesis site causes translation of the ball 104 to expel the obstruction O from the anchoring member 102 of the implant 100. This same approach may be used with many of the alternative valve implant designs described herein.

Referring to FIGS. 12A-12D, a method for removing a venous valve prosthesis 72A is illustrated. Before describing the removal method, however, it is noted that the embodiment of the venous valve prosthesis 72A differs from the embodiment 70 of FIGS. 9A-9C in one important regard. The venous valve prosthesis 72A is designed for retrieval and removal, in case of a non-functioning implant. In this embodiment, the anchoring member 74 of the implant 72A may optionally include barbs 80 only at the second end 78 (or "downstream" or "proximal" end), and thus the implant 72A may be removed in entirety. The barbs 80 prevent migration of the prosthesis 72A in the downstream direction, toward the heart. Migration of the prosthesis 72A distally (i.e., away from the heart) is less of an issue, since the vein diameter narrows as it proceeds distally.

With that introduction, in one embodiment, venous valve prosthesis removal may be performed using a removal device 110 that includes an outer sheath 112, an inner funnel catheter 114 with a funnel tip 116, and a hook 118 disposed within the funnel catheter 114. The funnel catheter 114 includes a thin, self-expanding polymeric funnel tip 116 on its distal end, which may be collapsed within the outer sheath 112 for intravenous delivery (FIG. 12B) and then expands upon exiting the sheath 112 (FIG. 12A). The funnel 116, catheter 114, and outer sheath 112 may be constructed of PTFE, nylon, polyethylene, or similar material(s). The hook 118 (e.g., stainless steel) lies inside the catheter lumen. For valve prosthesis removal, the catheter 112 is brought into proximity with the distal end of the prosthesis 72A, and the sheath 112 is retracted to deploy the funnel 116. The funnel 116 is advanced to mate with the distal tapered end of the prosthesis 72A, and the hook 118 is advanced then retracted to hook the valve seat 86 inside the distal end 76 of the prosthesis 72A (FIG. 12C). Then, as illustrated in FIG. 12D, the catheter 114 is retracted fully into the outer sheath 112, pulling the anchoring member 74 into the sheath 112 for valve removal. This same approach may be used with many of the alternative valve implant designs described herein.

It is typically difficult or impossible to remove an implanted frame, whether a metallic stent or a vena cava filter, from a blood vessel such as a vein. The removable prosthesis 72A described above may be retrieved within weeks or even a few months following implantation. Beyond that, fibrous ingrowth occurs into the anchoring member 74, which prevents its removal from the vein. Therefore, in some embodiments, the inner, ball valve portion of the venous valve prosthesis may be removed from the implant, while leaving the outer, anchoring member/frame portion intact within the vein. A method for removing the inner, ball valve portion may involve mating the deployment funnel with the proximal end of the prosthesis, using graspers or small scissors to cut the retaining feature (suture), and using graspers or suction to remove the ball portion of the implant. This same approach may be used with many of the alternative valve implant designs described herein.

Figure 13A:
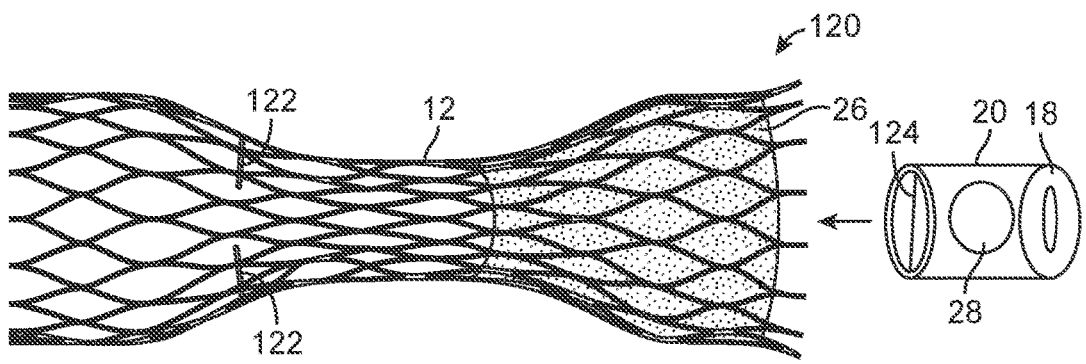
FIGS. 13A-13C are side views of a venous valve, illustrating insertion and removal of a central portion of the valve into and out of an implantable frame anchoring member, according to one embodiment.
Figure 13B:
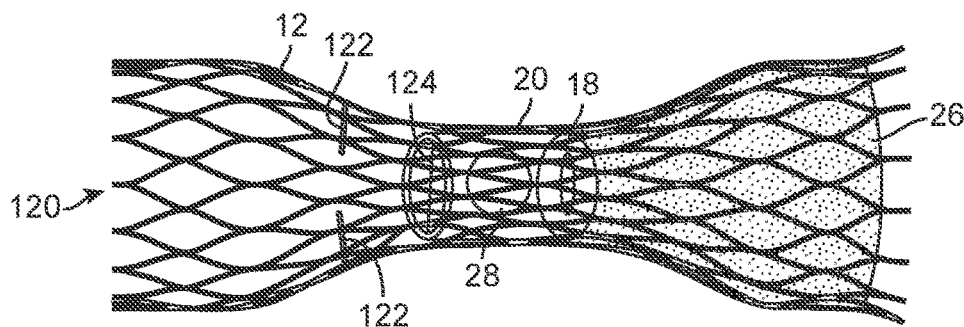
Figure 13C:
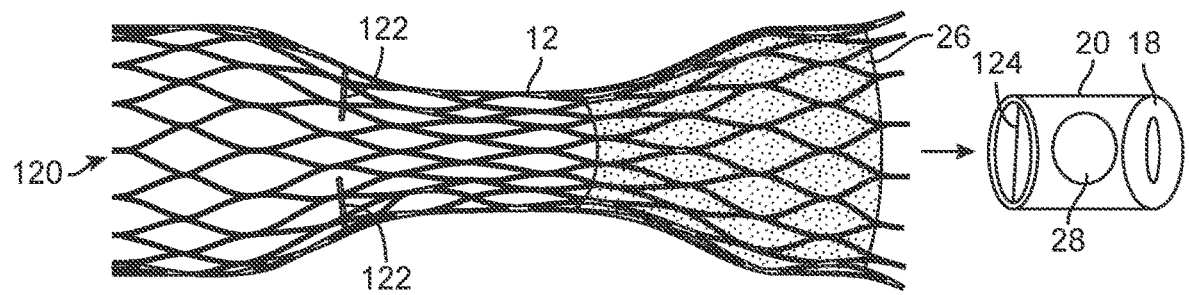

Referring now to FIGS. 13A-13C, the type of removal method just described is illustrated, although without a specific removal device being shown. In this embodiment, a venous valve prosthesis 120 includes the anchoring member 12 and the tubular frame 20, with the valve seat and a retention member 124. The anchoring member 12 also includes multiple stops 122, which are configured to stop the tubular frame 20 from passing out of the prosthesis 120 in the downstream direction. In this embodiment, the tubular frame 20 and ball 28 (or the "inner ball valve portion") of the venous valve prosthesis 120 may be removed from an outer anchoring member 12, so that the anchoring member 12 remains in place within the vein, and the valve portion can be repaired or removed and then optionally reinserted into the anchoring member 12. This method sequence is illustrated in FIG. 13A (insertion of ball valve portion into anchoring member 12), 13B (ball valve portion within anchoring member 12), and 13C (removal of ball valve portion). This method of repair may be used months or even years following implantation. The central portion of the elastic, self-expanding anchoring member 12 may contain an inner diameter slightly smaller than the outer diameter of the ball valve portion of the prosthesis 120. Therefore, when the ball valve portion is inserted into the anchoring member 12, the central portion of the frame exerts a compressive force on the outer surface of the ball valve portion to hold it in position. Stops 122 (or "tabs") on the proximal and/or distal end of the central portion of the anchoring member 12 may be configured to hold the ball valve portion and prevent it from migrating out of the frame. Venous return flow tends to push the ball valve portion proximally out of the anchoring member 12 towards the heart. The presence of stops 122 in this position will prevent such migration. The tubular frame 20 may be rigid or relatively flexible, according to various embodiments. A rigid tubular frame 20 may be constructed of metal, such as stainless steel, or a plastic material, such as polycarbonate. A flexible tubular frame 20 may be constructed of a polymer such as nylon, PTFE (polytetrafluoroethylene), or polyolefin. A flexible tubular frame 20 provides the benefit of additional compression, allowing it to be packed into a smaller catheter size desirable for use in implantation. This same approach may be used with many of the alternative valve implant designs described herein.

Figure 14A:
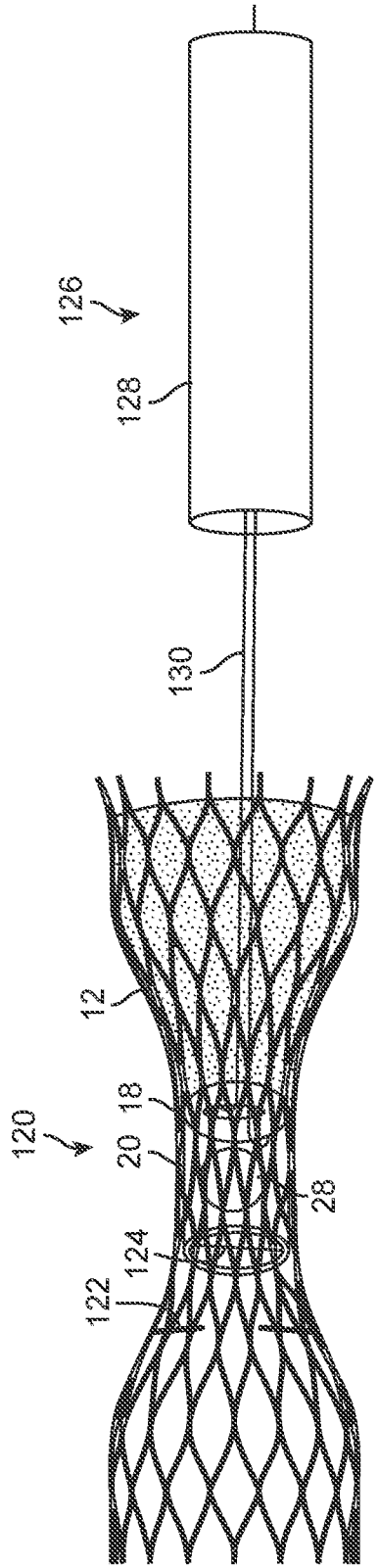
FIGS. 14A and 14B are side views of the valve of FIGS. 13A-13C, illustrating a device and method for removing the central portion of the valve from the implantable frame, according to one embodiment.
Figure 14B:
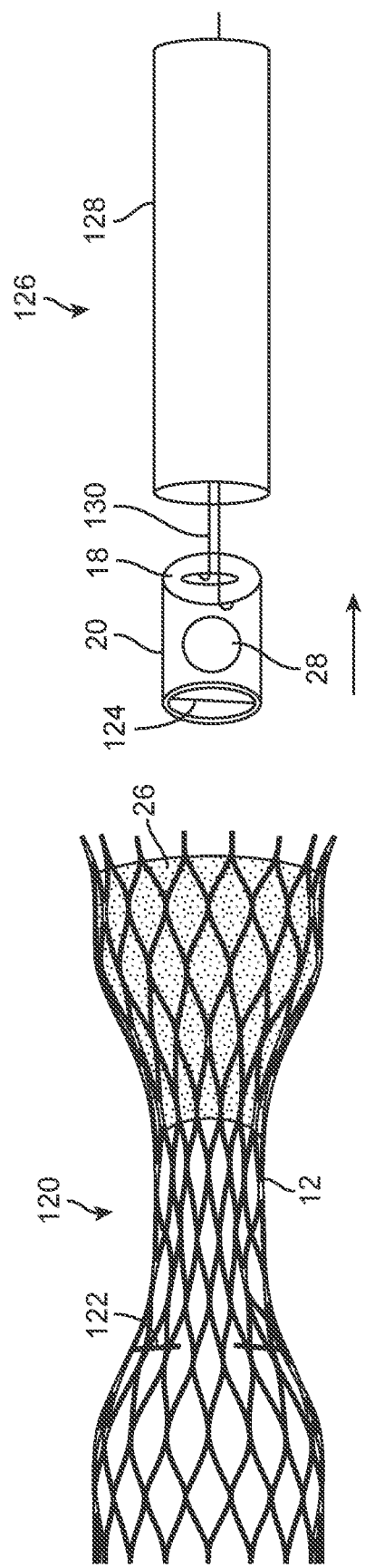

As illustrated in FIGS. 14A and 14B, removal of the ball valve portion of the prosthesis 120 may be accomplished using a removal device 126 that includes a catheter 128 containing one or more stainless steel hooks 130 that are advanced out of the catheter 128 and used to grasp the valve seat 18. The shafts of the hooks 130 lie inside a lumen that runs nearly the full length of the catheter 128. The hooks 130 are retracted into the distal end of the catheter 128 until the catheter 128 is advanced in proximity of the valve prosthesis 120. Then the hooks 130 are advanced and used to grasp the valve seat 18 (FIG. 14A), and the removal device 126 is pulled out of the vein to retrieve the ball valve component (FIG. 14B). Although the ball valve component is shown outside of the catheter 128 in FIG. 14B, this is shown this way only for purposes of illustration. Typically, the retrieval method would involve pulling the ball valve component into the catheter 128 while the distal end of the catheter 128 is located inside of the prosthesis. The removal device 126 would then be pulled out of the prosthesis 120 with the ball valve component inside of it, and the removal device 126 and ball valve component would then be withdrawn from the vein. In an alternative embodiment, the removal device 126 may employ suction rather than hooks 130 to remove the valve implant 120. This same approach may be used with many of the alternative valve implant designs described herein.

Figure 15:
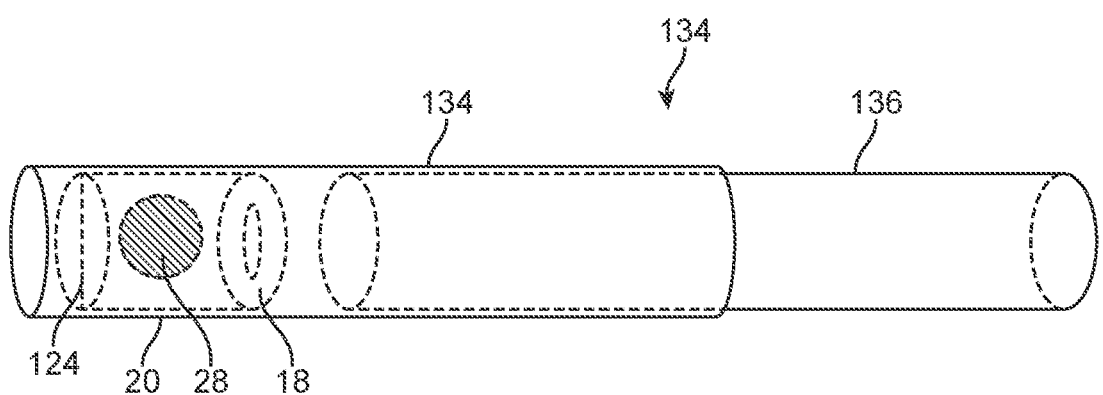
FIG. 15 is a perspective view of a delivery device for delivering the central portion of a prosthetic venous valve implant into an anchoring member of the implant, as in FIG. 13A, according to one embodiment.

Referring to FIG. 15, once the old ball valve component has been removed from the anchor frame 12, a new ball valve portion may be inserted, by means of a delivery device 132 that includes a catheter 134 and an inner plunger 136 that advances the ball valve portion into the implanted anchor frame 12. This same approach may be used with many of the alternative valve implant designs described herein.

Figure 16A:
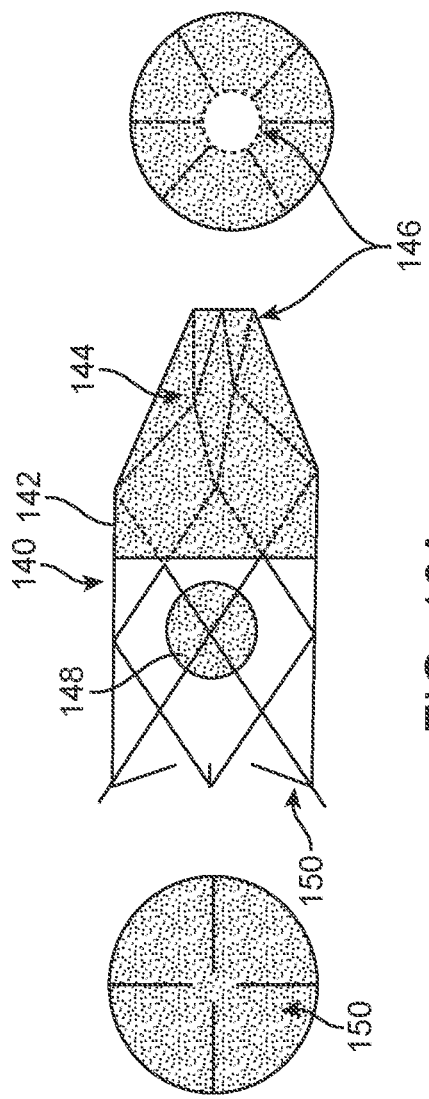
FIGS. 16A and 16B are side and end views of a prosthetic venous valve implant, according to another alternative embodiment.
Figure 16B:
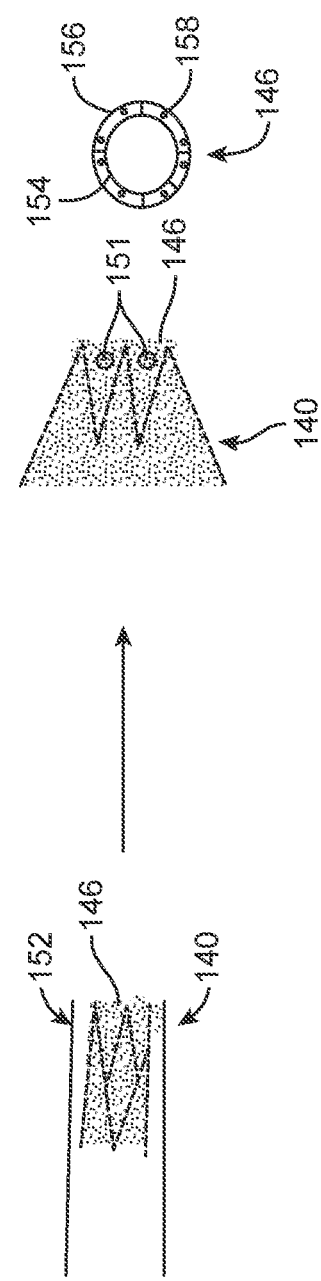

Referring now to FIGS. 16A and 16B, yet another alternative embodiment of a venous valve prosthesis 140 is illustrated. In this embodiment, a ball retention feature 150 includes multiple struts incorporated into the superelastic metal frame 142 and angled into the lumen of the prosthesis 140. The opening formed by the retention struts 150 is smaller than the diameter of the ball 148, thereby preventing exit of the ball 148 throughout the life of the valve 140. Another feature of this embodiment of the venous valve prosthesis 140, which may also be applied to other embodiments described herein, is the configuration of the valve seat 146. As illustrated in the right-most panel of FIG. 16B, the valve seat may include two flexible rings—an inner flexible ring 154, residing inside the covered superelastic frame 142, and an outer flexible ring 156, residing outside the covered frame 142. Multiple posts 158 extend through holes in the covering of the frame 142, which structurally connect the inner ring 154 to the outer ring 156. The inner ring 154 forms a seal with the ball 148 upon contact. The inner ring 154, outer ring 156 and connecting posts 158 may be formed of an elastomer, such as silicone rubber, molded into the distal end of the covered superelastic frame 142. Multiple holes 151 may be disposed around the circumference of the sealing membrane 144 near the distal end of the frame 142 (FIG. 16B, middle panel). The configuration of the inner ring 154, outer ring 156 and connecting posts 158 helps ensures that the valve seat 146 is not distorted following valve deployment, to maintain an adequate seal against the ball. As illustrated in the left-most panel of FIG. 16B, the valve seat 146 may be distorted while the valve 140 resides within a delivery sheath 152. Upon exit from the delivery sheath 152, the connecting posts 158 exert tension on the inner ring 154 that forms the valve seat 146, to restore it to its symmetrical functional geometry. This valve seat 146 may may be used with many of the alternative valve implant designs described herein.

Referring to FIGS. 16C and 16D, in an alternative embodiment, the valve seat 147 of the venous valve prosthesis 140 may be formed by bonding a ring to the inner surface of the sealing membrane 144 that covers the superelastic frame 142, near the distal end of the implant 140. The inner ring 154 of the valve seat 147 (FIG. 16D, right-most panel) may be composed of the same material as that of the sealing membrane 144, for example PTFE or nylon. Circumferential attachment of the inner ring 154 to the sealing membrane 144 ensures that the valve seat 147 is not distorted upon valve exit from the delivery sheath 152. This valve seat 147 may be used with many of the alternative valve implant designs described herein.

Figure 17A:
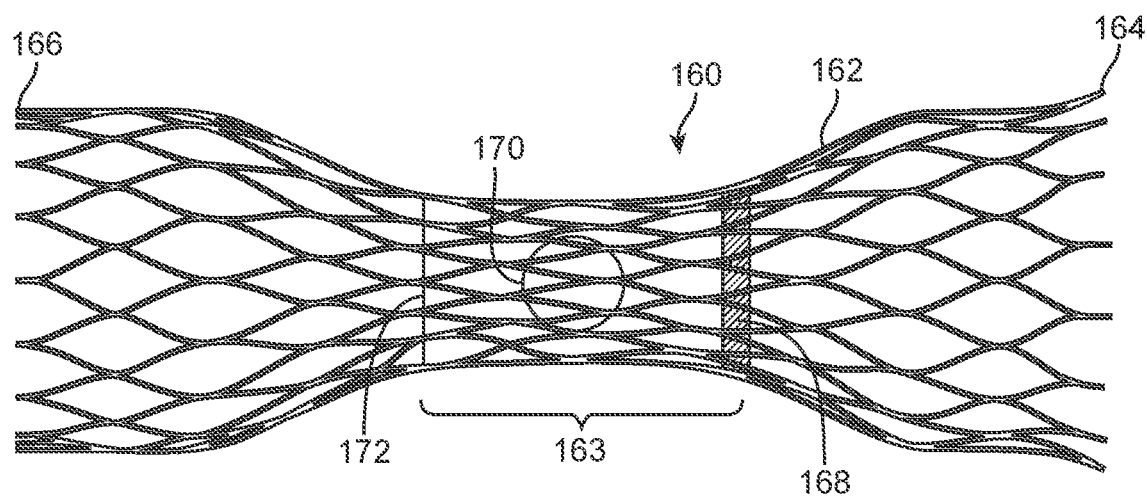
FIGS. 17A and 17B are side and end views, respectively, of a prosthetic venous valve implant, according to another alternative embodiment.
Figure 17B:
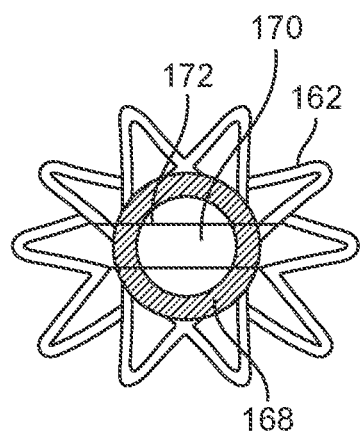

Referring now to FIGS. 17A and 17B, in another embodiment, a venous valve prosthesis 160 may include an anchoring member 162 (or "frame"), with a first end 164, a second end 166, and a middle valve portion 163. Inside the anchoring member 162 are a ball 170, a valve seat 168 and a retention member 172. In this embodiment, there is no inner tubular frame. Instead, the first and second ends 164, 166 of the anchoring member 162 expand to anchor the implant 160 within a vein, and the middle valve portion 163 maintains a smaller diameter and acts as a substantially tubular holder for the ball 170. As discussed above, the anchoring frame 162 may be made of continuous superelastic material, such as Nitinol, which may be entirely or partially coated in a material, such as PTFE, silicone, or hyaluronic acid. This coating funnels blood through the central valve component. The retention member 172 may include multiple pieces of crossing suture, which extend across the lumen of the implant in any suitable pattern or configuration. The entire implant 160 may be compressible (ball 170, valve seat 168, anchoring frame 162, retainment feature 172), so that it can be packed into a small delivery catheter to facilitate ease of implantation. Any valve seat, ball, anchor feature such as barbs, or retainer embodiment described in this application may be used in this embodiment. External compression and/or a ferromagnetic ball and externally placed magnet may also be applied with this embodiment, for clearance of clot. Removal of the entire device 160, or just the ball 170, is also possible. The same deployment funnel may be mated with the proximal end of the prosthesis 160, using the graspers or small scissors to cut the retention member 172, and using graspers or suction to remove the ball 170 from the valve 160.

Figure 18A:
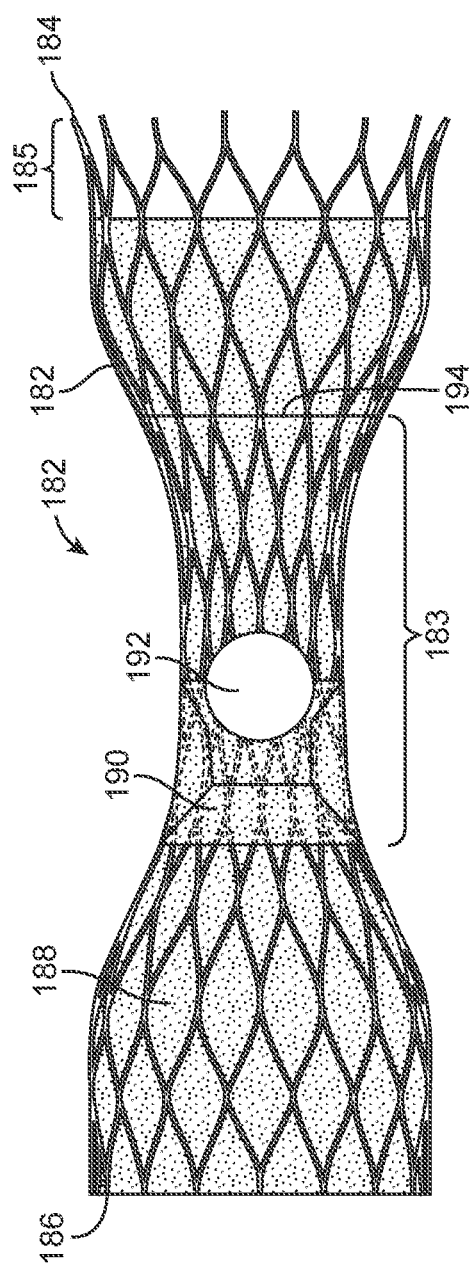
FIGS. 18A and 18B are side, cross-sectional views of a prosthetic venous valve implant with a straight middle portion design, according to one embodiment.
Figure 18B:
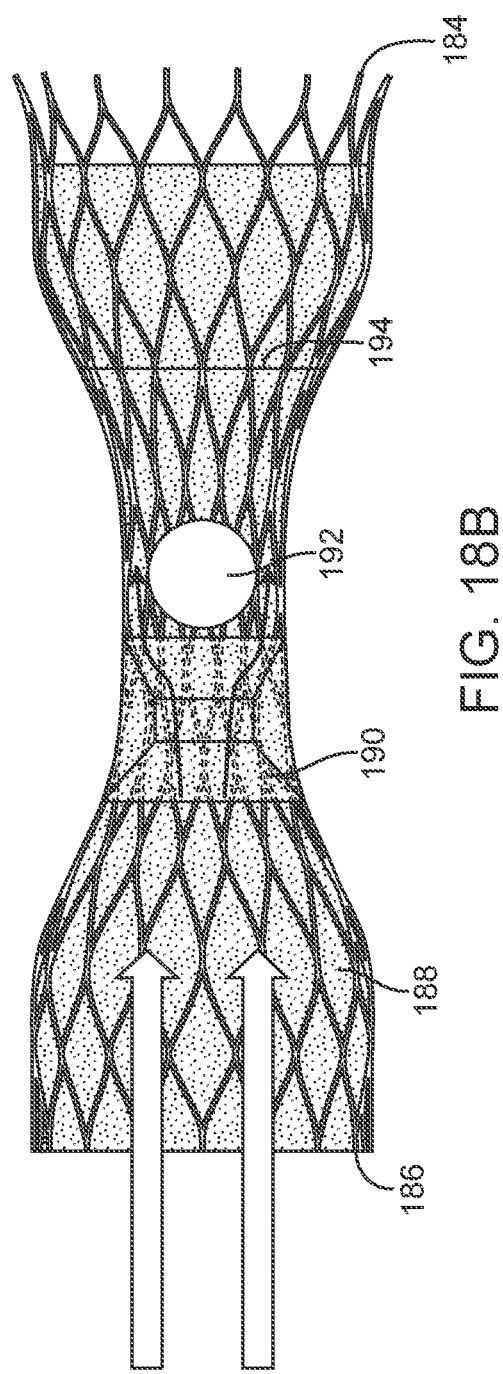
Figure 19C:
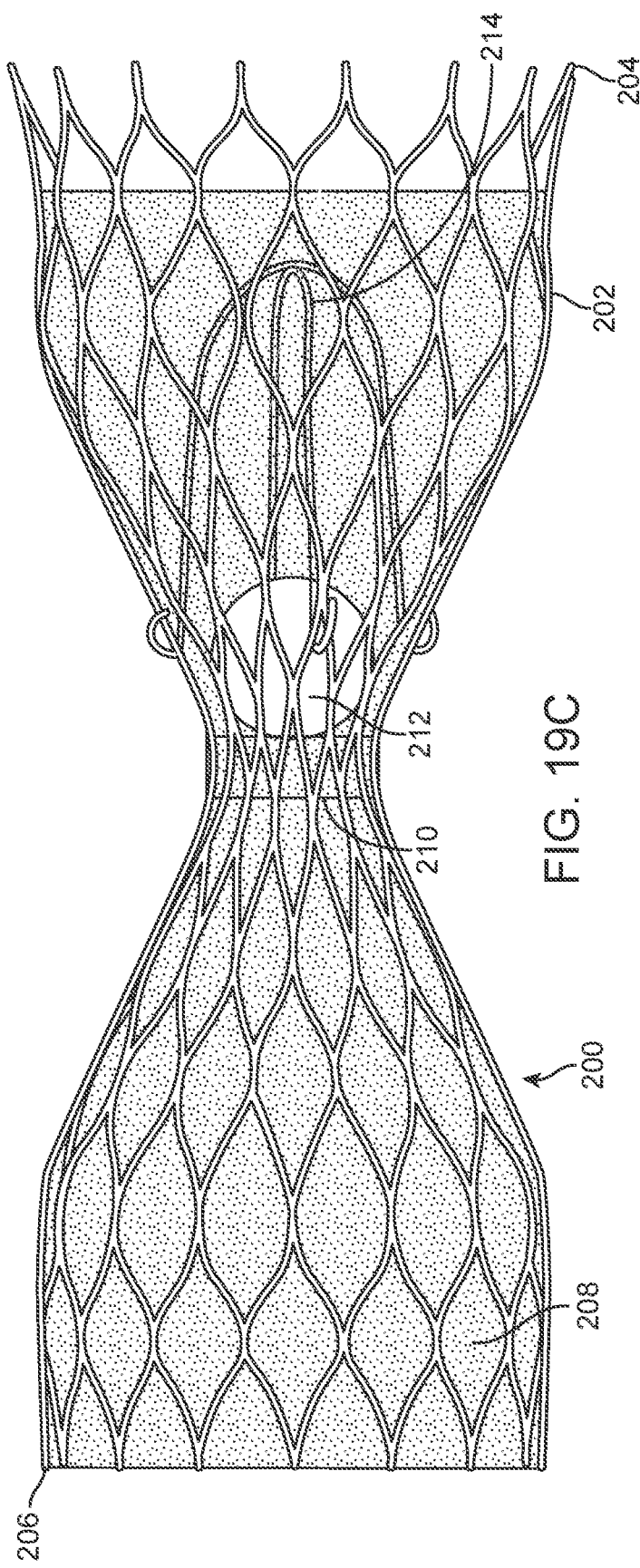
FIGS. 19C and 19D are side and partial/magnified views, respectively, of the venous valve implant of FIGS. 19A and 19B, illustrating further detail of a ball retention cage attachment to an anchoring member, according to one embodiment.
Figure 19D:
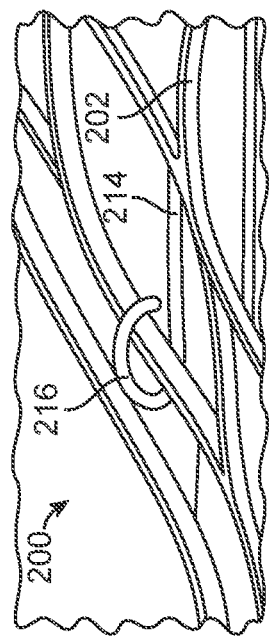

Referring now to FIGS. 18A and 18B, in another alternative embodiment, a prosthetic venous valve implant 180 may include an anchoring member 182 for anchoring the implant within a vein, such as a self-expanding, tubular frame that forms a lumen and is partially or completely covered with a membrane 188. In this embodiment, the anchoring member 182 has a first end 186 (or "upstream" or "distal" end), a second end 184 (or "downstream" or "proximal" end), a middle valve portion 183, and an optionally uncovered portion 185 immediately adjacent the second end 184. The valve implant 180 also includes a ball 192, a valve seat 190, and a ball retention member 194. The valve seat 190 is closer to the first end 186 than to the second end 184, and the retention member 194 is closer to the second end 184 than to the first end 186. In this embodiment, the valve seat 190 and ball retention member 194 are located at or near opposite ends of the middle valve portion 183, but they may have other locations within the anchoring member 182 in alternative embodiments. When fully expanded, anchoring member 182 has a generally hourglass shape, although with a relatively straight, tubular middle valve portion 183, and is designed to anchor the valve implant 180 to the luminal surface of the vein. (In alternative embodiments, described below, the middle valve portion itself may have an hourglass shape rather than being straight.) The ball valve portion of the implant 180 acts as the venous valve. Optionally, all or a portion of the self-expanding frame 182 may be coated or otherwise covered with a hemostatic membrane 188. FIG. 18A shows the implant 180 with the ball 192 seated in the valve seat 190, which may be referred to as the closed position, to prevent backflow of blood through the valve in a retrograde direction. FIG. 18B shows the ball 192 moving out of the valve seat 190, toward the ball retention member 194 and thus toward an open position, as occurs with the flow of blood through the valve implant 180.

In this embodiment, the ball 192, valve seat 190 and ball retention member 194 may have any of the features and configurations described above in relation to any of the other described embodiments. The ball 192, in the illustrated embodiment, has a spherical shape, although an ovoid ball or other shape of ball may also be used, and the ball 192 may also have dimples, grooves, slits, or any other surface features previously mentioned. The ball 192 may also be made of any suitable material or materials and may be rigid, flexible, solid or hollow. In some embodiments, the ball 192 has a density that is slightly greater than that of blood (1.06 grams/cubic centimeter), for example between 1.2 grams per cubic centimeter and 2.5 grams per cubic centimeter. With the ball 192 having this density, the valve 180 functions with both a low opening pressure and a low closing pressure. The ball 192 may be constructed of any suitable material, such as but not limited to PTFE (polytetrafluoroethylene), silicone rubber, silastic rubber, silicone, stainless steel, Teflon, and the like. Optionally, an anti-coagulant agent, such as heparin, or another coating, such as hyaluronic acid, may be bonded to the surface of the ball 192. The ball 192 may contain a core of with a material of different density and properties (e.g. ferromagnetic) covered in another material (e.g. polymer such as PTFE).

In some embodiments, the ball 192 may have a ball diameter such that the distance between the valve seat 190 and the ball retention member 194 is between two times and four times greater than the ball diameter. The ball diameter may also be sized such that the ball 192 contacts an inner surface of the middle valve portion 183 as the ball 192 travels back and forth between the valve seat 190 and the ball retention member 194, so that contact between the ball 192 and the middle valve portion 183 is able to dislodge substances that form on or cling to the middle valve portion 183. This sizing of the ball 192 and the diameter of the middle valve portion 183 thus may impart a "self-cleaning" ability to the implant device 180. For example, in some embodiments, the ball 192 may have a diameter of between 0.5 mm and 30 mm. More specifically, in some embodiments, the ball 192 may have a diameter between 1 mm and 8 mm.

The valve seat 190 may be formed of toroidal elastomer, silicone rubber, Nitinol, or any other material. In some embodiments, the valve seat 190 and the anchoring member 182 may be made of the same material, such as Nitinol in one embodiment. The valve seat 190 may be rigid (e.g., stainless steel, Nitinol, or polycarbonate) or flexible/collapsible (e.g., silicone), to facilitate packing into a smaller delivery sheath. In some embodiments, an inner surface of the valve seat 190 may be coated in the same continuous material 188 lining the anchoring member 182, to limit or prevent luminal or blood exposure. The valve seat 190 may expand to a diameter greater than that of the delivery sheath and/or vein wall to maximize flow-through area. The valve seat 190 may be permanent or replaceable.

The ball retention member 194 may be formed as a circular constriction, one or more pieces of suture or wire that cross the lumen of the anchoring member 182, one or more arches that cross the lumen of the anchoring member 182, or any other suitable feature or features for stopping or retaining the ball 192 from passing through the valve implant 180 in the downstream direction. The ball retention member 194 may be made of any biocompatible material, such as but not limited to stainless steel, titanium, Nitinol, stellite, silicone, or the like.

As mentioned above, the anchoring member 182 may be a self-expanding or balloon expandable, anchoring frame, having a stent-like lattice structure. In this embodiment, the first or upstream end 186 and the second or downstream end 184 expand to greater diameters than the middle valve portion 183 of the anchoring member 182. The two ends 186, 184 typically dilate a vein or other vessel into which they are implanted. In some embodiments, the middle valve portion 183 also expands upon delivery to a diameter sufficient to dilate the vein. In some embodiments, the implant 180 also includes the membrane 188 (or "coating") disposed over part of the anchoring member 182. This coating 188 may act as a hemostatic barrier that funnels blood through the central lumen of the device 180. The coating 188 may consist of a hemostatic material, such as a polymer (e.g. PTFE, silicone, PET, nylon, or hyaluronic acid), and may further be infused or bonded with heparin, hyaluronic acid, or other agent. The hemostatic membrane 188 covering the inlet and/or outlet sections of the superelastic wire frame 182 can seal against the inner vein wall to prevent or reduce leakage around the outside of the implant 180. Additionally, the extreme downstream end 184 may expand to a slightly larger diameter than an immediately adjacent downstream portion, thus forming a wider expandable portion 185 which may also be uncovered/uncoated. With this extra expansion, the downstream end 184 may form multiple anti-migration tips when the anchoring member 182 is expanded. These tips may help prevent downstream migration of the implant 180 within a vein. Optionally, and not shown in FIGS. 18A and 18B, some embodiments may include additional anti-migration barbs on the anchoring frame 182.

The anchoring member 182 may be a frame constructed of an engineered polymer (i.e., PEEK, Polypropylene, PTFE, etc.), stainless steel, or a superelastic metal, such as Nitinol. A Nitinol tube may be laser cut in a lattice pattern, and its proximal and distal sections (or "downstream and upstream sections," respectively) may be expanded, while its center section (or "middle valve portion 183") may be retained in a smaller diameter. In some embodiments, the proximal and distal sections of anchoring member 182 may be expanded to between 0.1 mm and 100 mm. More specifically, some embodiments may have proximal and distal sections expanded to between 10 mm and 20 mm. In some embodiments, the length of the anchoring member 182 may be between 1 mm and 200 mm, with some embodiments between 20 mm to 40 mm. In some embodiments, the central narrowed middle valve portion 183 may have a diameter between 1 mm and 100 mm, and a length between 0.1 mm and 100 mm. More specifically, in some embodiments the middle valve portion 183 may have an outer diameter between 3 mm and 20 mm, and a length between 5 mm and 15 mm. The anchoring member 182 may be self-expandable from a collapsed configuration, for delivery through a delivery catheter, and have an expanded configuration upon release from the delivery catheter. Alternatively, the anchoring frame may be balloon expandable. The upstream end 186 and the downstream end 184 of the anchoring frame 182 may be sized to dilate the vein when the implant 180 is implanted in the vein. The middle valve portion 183 of the anchoring frame may also sized to dilate the vein when the implant 180 is implanted in the vein. The middle valve portion 183 may have a mostly straight configuration, as in FIGS. 18A and 18B, or may have an hourglass shape, as described further below. Other cleaning features, such as external compressibility, magnetic manipulation of the ball, removing the ball 192 or valve seat 190, or removing the entire device 180, as described elsewhere in this application, may be applied to this embodiment.

Referring now to FIGS. 19A-19D, another embodiment of a venous valve implant 200, with a diverging valve body design, is illustrated. In this embodiment, the implant 200 includes an anchoring member 202 with an upstream end 206 and a downstream end 204, a membrane 208 covering part of the anchoring member 202, a valve seat 210, a ball retention member 214, and a ball 212. Many of these components are the same as in the embodiment described in relation to FIGS. 18A and 18B, so these will not be described again. In this embodiment, however, the middle portion of the anchoring member 202 is hourglass shaped, rather than straight. This configuration makes the flow area around the ball 212, as the ball moves away from the valve seat 210 (FIG. 19B), significantly greater than in the straight valve design of FIGS. 18A and 18B. In this embodiment, the ball retention member 214 is configured as a cage of U-shaped members with hooks 216 (FIG. 19D) that attach to the anchoring member 202. In this embodiment, the ball retention member 214 includes two U-shaped members attached to, and extending across the lumen of, the anchoring member 202.

FIGS. 20 and 21 illustrate additional alternative embodiments of prosthetic venous valve implants. In the embodiment of FIG. 20, the implant 220 includes an anchoring member 222, a valve seat 224, a ball 228, and a ball retention member 226. In this embodiment, the ball retention member 226 includes two, crossing, U-shaped members that are attached to the outside surface of the anchoring member 222, around the valve seat 224. A ring 227 holds the U-shaped members in place around the anchoring member 222. Otherwise, all of the components and features of the implant 220 are the same or similar to those of embodiments described above.

In the embodiment of FIG. 21, the implant 230 includes an anchoring member 232, a valve seat 234, a ball 238, and a ball retention member 236. In this embodiment, the ball retention member 236 includes two, crossing, U-shaped members that are attached to the inside surface of the valve seat 234. Otherwise, all of the components and features of the implant 230 are the same or similar to those of embodiments described above.

Figure 23A:
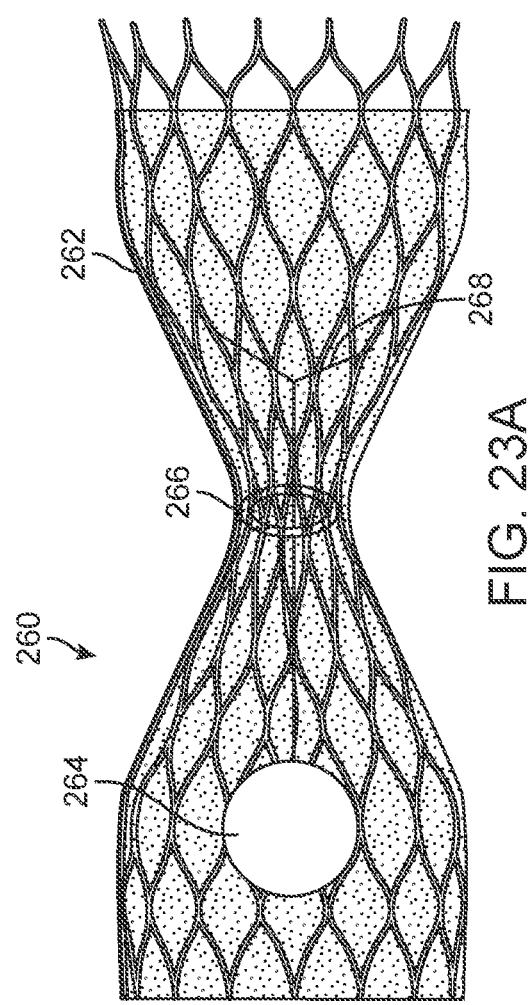
FIGS. 23A and 23B are diagrammatic side views of two different embodiments of a prosthetic venous valve implant, each including a different embodiment of a ball retention member.
Figure 23B:
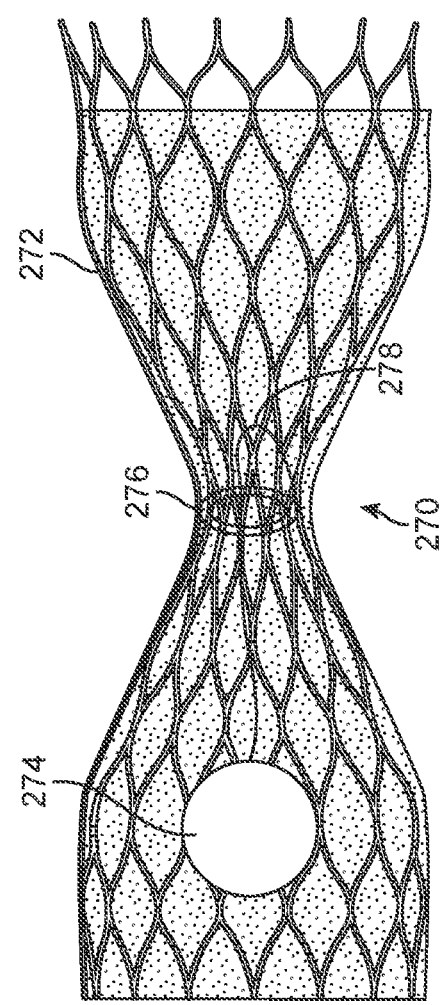

FIGS. 23A and 23B illustrate two additional alternative embodiments of a prosthetic venous valve implant. In the embodiment of FIG. 23A, the implant 260 includes an anchoring member 262, a ball 264, a valve seat 266, and a retention member 268. In this embodiment, the retention member 268 is an expandable wire anchor, attached to the ball 264, rather than a stop member attached to an anchoring member, as in previously described embodiments. The retention member 268 stops the ball 264 from passing out of the valve implant 260 in the downstream direction.

In the embodiment of FIG. 23B, the implant 270 includes an anchoring member 272, a ball 274, a valve seat 276, and a retention member 278. In this embodiment, the retention member 278 is a tether, attaching the ball 274 to the valve seat 276. The retention member 278 may be made of suture, wire such as Nitinol, or the like. Again, the retention member 278 stops the ball 274 from passing out of the valve implant 270 in the downstream direction. Either of these two retention members 268, 278 may be applied in other embodiments described herein.

Although the above description is believed to be complete and accurate, various changes may be made to any of the embodiments described herein, without departing from the scope of the invention as it is set forth in the claims. For example, features of one described embodiment may be employed in other embodiments, features may be eliminated from or added to a given embodiment, or the like, without departing from the scope. Therefore, the above description should be used for explanatory and exemplary purposes only and should not be interpreted as limiting the scope of the invention as defined by the claims.

What is claimed is:

1. A method for treating a peripheral vein, the method comprising:
    deploying a venous valve prosthesis out of a distal end of a catheter and into the peripheral vein, wherein after exiting the catheter a tubular anchoring frame of the venous valve prosthesis expands within the peripheral vein and contacts an inner wall of the peripheral vein to maintain the venous valve prosthesis within the peripheral vein, and wherein a ball inside the tubular anchoring frame moves between an open position, in which the ball is positioned to allow forward flow of blood through the venous valve prosthesis, and a closed position, in which the ball contacts a valve seat, to prevent or reduce backflow of blood through the venous valve prosthesis;
    removing the catheter from the peripheral vein, leaving the venous valve prosthesis in place within the peripheral vein to help facilitate blood flow through the peripheral vein; and
    after a determination has been made that there is a need to remove the ball from the venous valve prosthesis, collapsing and removing the ball from the venous valve prosthesis, while leaving at least the tubular anchoring frame in the peripheral vein.

2. The method of claim 1, further comprising dilating the peripheral vein with at least one of a first end or a second end of the tubular anchoring frame.

3. The method of claim 2, further comprising dilating the peripheral vein with a middle portion of the tubular anchoring frame, between the first end and the second end.

4. The method of claim 1, wherein the ball has a diameter configured so that the ball contacts an inner surface of the tubular anchoring frame as it moves back and forth between the open position and the closed position.

5. The method of claim 1, further comprising applying external compression to the venous valve prosthesis from outside the peripheral vein, to expel an obstruction out of the venous valve prosthesis.

6. The method of claim 1, wherein the ball comprises a magnetic material, and wherein the method further comprises moving a magnet outside of the venous valve prosthesis to cause the ball to move back and forth within the tubular anchoring frame to expel an obstruction out of the venous valve prosthesis.

7. The method of claim 1, further comprising replacing the removed ball with a new ball.

8. The method of claim 1, wherein the venous valve prosthesis further comprises a ball retention tether, comprising:
    a first portion attached to the ball; and
    a second portion attached to at least one of the tubular anchoring frame or the valve seat.

9. The method of claim 1, wherein the venous valve prosthesis further comprises a ball retention wire anchor, comprising:
    a first portion attached to the ball; and
    an expandable portion disposed upstream of the valve seat and having an expanded diameter wider than a diameter of the valve seat, such that the expandable portion is wide enough that it cannot pass through the valve seat.

10. The method of claim 1, wherein the ball has a shape selected from the group consisting of spherical, ovoid, oblong, asymmetrical, cylindrical, cylindrical with a pointed end, rhomboid and cylindrical with a rounded end.

11. The method of claim 1, further comprising advancing the catheter through a previously implanted prosthesis before deploying the venous valve prosthesis.

12. The method of claim 1, wherein the ball is removed after an occlusion has occurred in the venous valve prosthesis or the ball has become non-functional.

13. The method of claim 1, wherein the valve seat is attached to the tubular anchoring frame.

14. The method of claim 13, further comprising removing the valve seat from the venous valve prosthesis, while leaving at least the anchoring frame of the venous valve prosthesis in the peripheral vein.

15. The method of claim 1, wherein the valve seat is integrally formed with the tubular anchoring frame.

16. A method for treating a vein, the method comprising:
    deploying a venous valve prosthesis out of a distal end of a catheter and into the vein, wherein the venous valve prosthesis comprises:
        a tubular expandable anchoring frame extending from a first end to a second end of the venous valve prosthesis, forming a lumen; and
        a collapsible ball in the lumen of the anchoring frame;
    wherein after deploying the venous valve prosthesis, the collapsible ball moves back and forth within the lumen between an open position in which the collapsible ball is positioned to allow forward flow of blood through the venous valve prosthesis, and a closed position upstream of the open position in which the collapsible ball prevents or reduces backflow of blood through the venous valve prosthesis; and
    wherein the collapsible ball is tethered to a location upstream of the collapsible ball at least when the collapsible ball is in the open position in its most downstream position.

17. The method of claim 16, further comprising dilating the vein with at least one of a first end or a second end of the anchoring frame.

18. The method of claim 16, further comprising:
after determining that there is a need to remove the collapsible ball from the venous valve prosthesis, untethering the collapsible ball; and
removing the collapsible ball from the venous valve prosthesis, while leaving the venous valve prosthesis in the vein.

19. The method of claim 18, further comprising replacing the removed collapsible ball with a new ball.

20. The method of claim 16, wherein the collapsible ball has a shape selected from the group consisting of spherical, ovoid, oblong, asymmetrical, cylindrical, cylindrical with a pointed end, rhomboid and cylindrical with a rounded end.

21. The method of claim 16, wherein the venous valve prosthesis comprises a valve seat formed by or attached to the anchoring frame.

22. The method of claim 21, wherein the collapsible ball is tethered to at least one of the anchoring frame or the valve seat.

\* \* \* \* \*